(12) United States Patent
Albert et al.

(10) Patent No.: US 7,594,924 B2
(45) Date of Patent: Sep. 29, 2009

(54) SPINAL STABILIZATION USING BONE ANCHOR SEAT AND CROSS COUPLING WITH IMPROVED LOCKING FEATURE

(75) Inventors: Todd James Albert, Narberth, PA (US); Rafail Zubok, Mindland Park, NJ (US); Mikhail Kvitnitsky, Clifton, NJ (US)

(73) Assignee: Accelerated Innovation, LLC, Clifton, NJ (US)

( * ) Notice: Subject to any disclaimer, the term of this patent is extended or adjusted under 35 U.S.C. 154(b) by 141 days.

(21) Appl. No.: 11/360,707

(22) Filed: Feb. 23, 2006

(65) Prior Publication Data

US 2006/0229616 A1 Oct. 12, 2006

Related U.S. Application Data

(60) Provisional application No. 60/658,227, filed on Mar. 3, 2005.

(51) Int. Cl.
*A61B 17/70* (2006.01)

(52) U.S. Cl. ......... 606/267; 606/300; 606/265; 606/279; 606/264

(58) Field of Classification Search ......... 606/61, 606/54, 57, 58, 59, 250, 272, 308, 319, 246, 606/266, 270, 278, 300, 301, 302, 303, 305, 606/306, 307, 309, 323, 251, 252, 253, 267, 606/254, 255, 256, 257, 258, 259, 260, 261, 606/262, 263, 264, 265, 268, 269, 271, 273, 606/274, 275, 276, 277, 279, 310, 311, 312, 606/313, 314, 315, 316, 317, 318, 320; 623/17.11, 623/17.12, 17.13, 17.14, 17.15, 17.16; 403/150, 403/157, 371, 362
See application file for complete search history.

(56) References Cited

U.S. PATENT DOCUMENTS 4,987,892 A * 1/1991 Krag et al. ............. 606/61

(Continued)

FOREIGN PATENT DOCUMENTS

WO WO2004/010881 A1 2/2004

OTHER PUBLICATIONS

International Preliminary Report on Patentability and Written Opinion for International Application PCT/US2006/006944.
ISR of PCT/US2006/06944, Feb. 23, 2006, Albert et al.

*Primary Examiner*—Eduardo C Robert
*Assistant Examiner*—Jan Christopher Merene
(74) *Attorney, Agent, or Firm*—Matthew B Dernier, Esq.; Gibson & Dernier LLP

(57) ABSTRACT

A stabilization rod engaging apparatus for implantation in a patient includes: a first pivot element including at least one first aperture, a first engagement element, and a first locking element; a second pivot element including at least one second aperture, a second engagement element, and a second locking element, wherein: the first and second apertures are sized, shaped and disposed in substantial axial alignment such that they are operable to receive the stabilization rod therethrough, and displacement of the first and second locking elements relative to one another urges the first and second apertures to misalign and thereby clamp the stabilization rod.

26 Claims, 19 Drawing Sheets

U.S. PATENT DOCUMENTS

| | | | |
|---|---|---|---|
| 5,344,422 A * | 9/1994 | Frigg | 606/278 |
| 5,360,431 A | 11/1994 | Puno et al. | |
| 5,474,555 A | 12/1995 | Puno et al. | |
| 5,584,831 A | 12/1996 | McKay | |
| 5,584,833 A | 12/1996 | Fournet-Fayard et al. | |
| 5,611,800 A * | 3/1997 | Davis et al. | 606/61 |
| 5,624,442 A | 4/1997 | Mellinger et al. | |
| 5,683,392 A * | 11/1997 | Richelsoph et al. | 606/272 |
| 5,810,819 A | 9/1998 | Errico et al. | |
| 6,187,005 B1 | 2/2001 | Brace et al. | |
| 6,210,413 B1 * | 4/2001 | Justis et al. | 606/254 |
| 6,302,888 B1 | 10/2001 | Mellinger et al. | |
| 6,309,390 B1 * | 10/2001 | Le Couedic et al. | 606/264 |
| 6,565,569 B1 | 5/2003 | Assaker et al. | |
| 6,663,635 B2 | 12/2003 | Frigg et al. | |
| 6,736,816 B2 * | 5/2004 | Ritland | 606/307 |
| 6,746,449 B2 | 6/2004 | Jones et al. | |
| 6,755,830 B2 | 6/2004 | Minfelde et al. | |
| 7,166,108 B2 * | 1/2007 | Mazda et al. | 606/305 |
| 7,166,109 B2 * | 1/2007 | Biedermann et al. | 606/279 |
| 7,211,087 B2 * | 5/2007 | Young | 606/61 |
| 7,220,262 B1 * | 5/2007 | Hynes | 606/61 |
| 7,270,665 B2 * | 9/2007 | Morrison et al. | 606/61 |
| 2003/0187439 A1 | 10/2003 | Biedermann et al. | |
| 2004/0039385 A1 | 2/2004 | Mazda et al. | |
| 2004/0092930 A1 | 5/2004 | Petit et al. | |
| 2004/0102781 A1 * | 5/2004 | Jeon | 606/73 |
| 2004/0147929 A1 | 7/2004 | Biedermann et al. | |
| 2004/0215190 A1 * | 10/2004 | Nguyen et al. | 606/61 |
| 2004/0243126 A1 | 12/2004 | Carbone et al. | |
| 2004/0254574 A1 | 12/2004 | Morrison et al. | |
| 2005/0010216 A1 | 1/2005 | Gradel et al. | |
| 2005/0049589 A1 | 3/2005 | Jackson | |
| 2005/0055026 A1 | 3/2005 | Biedermann et al. | |
| 2005/0131404 A1 * | 6/2005 | Mazda et al. | 606/61 |
| 2005/0187548 A1 | 8/2005 | Butler et al. | |
| 2005/0228375 A1 | 10/2005 | Mazda et al. | |

* cited by examiner

202

202

22

200

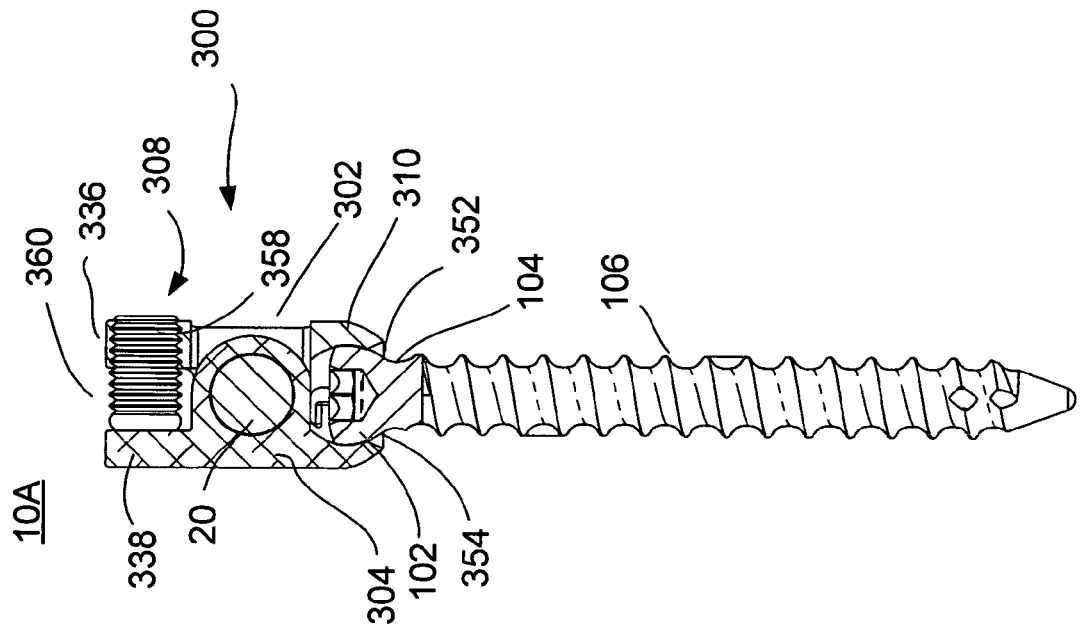
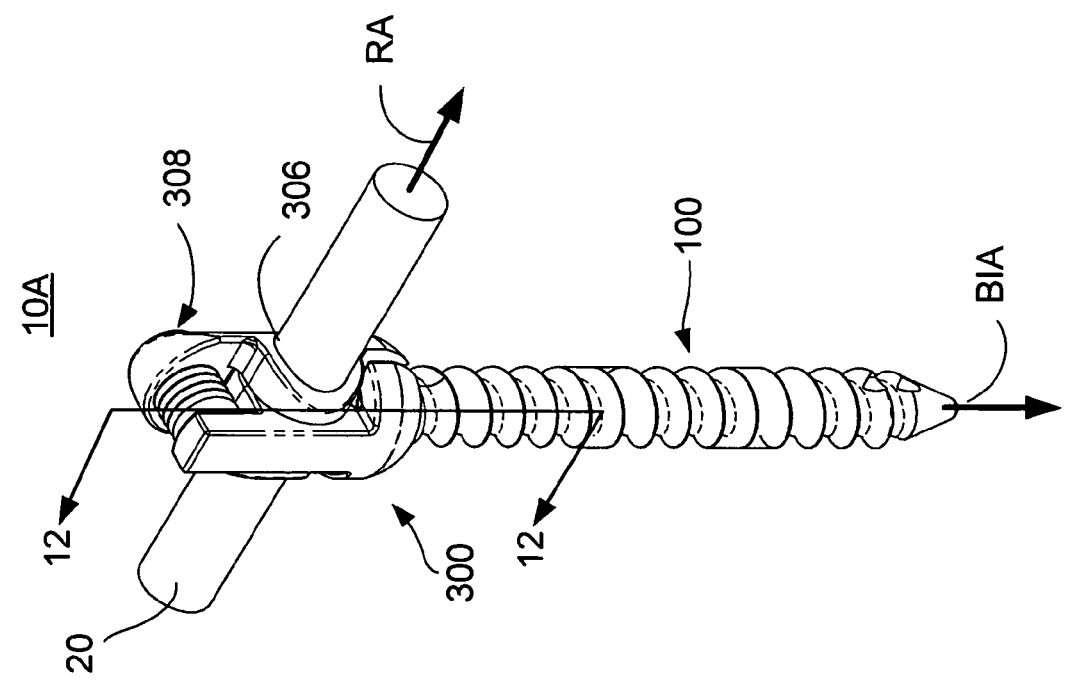

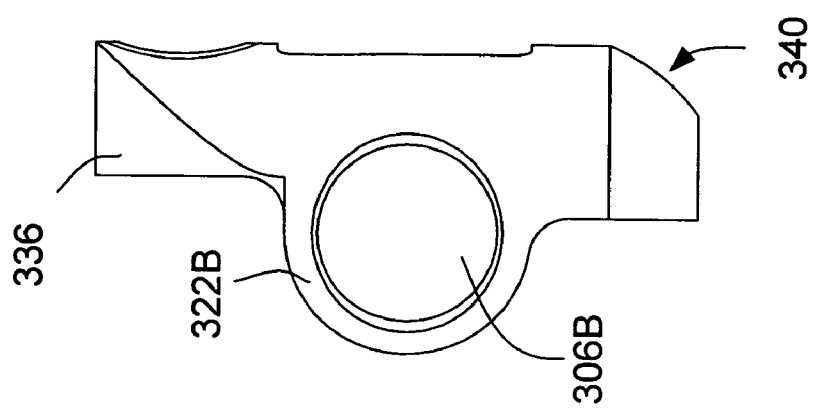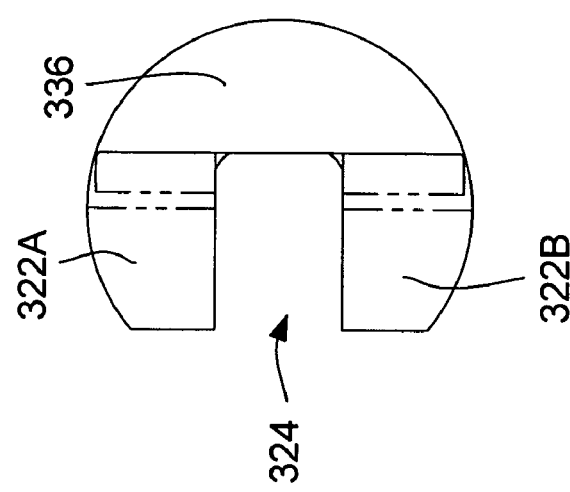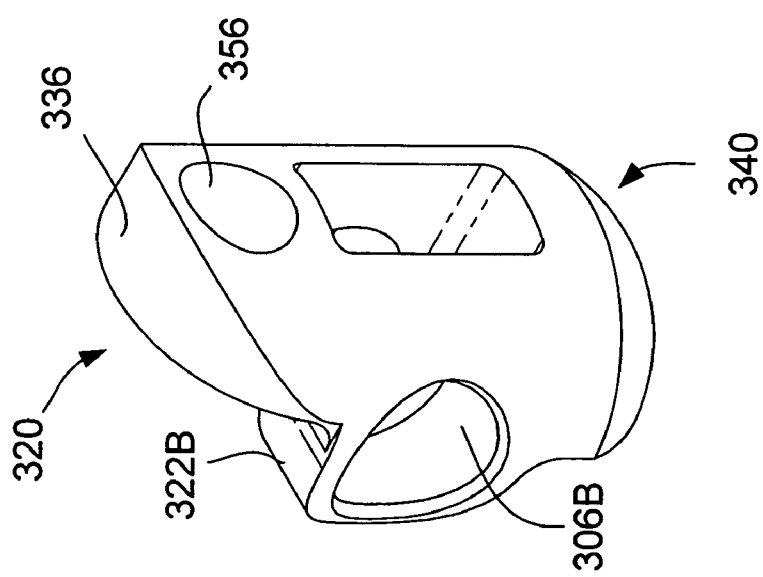

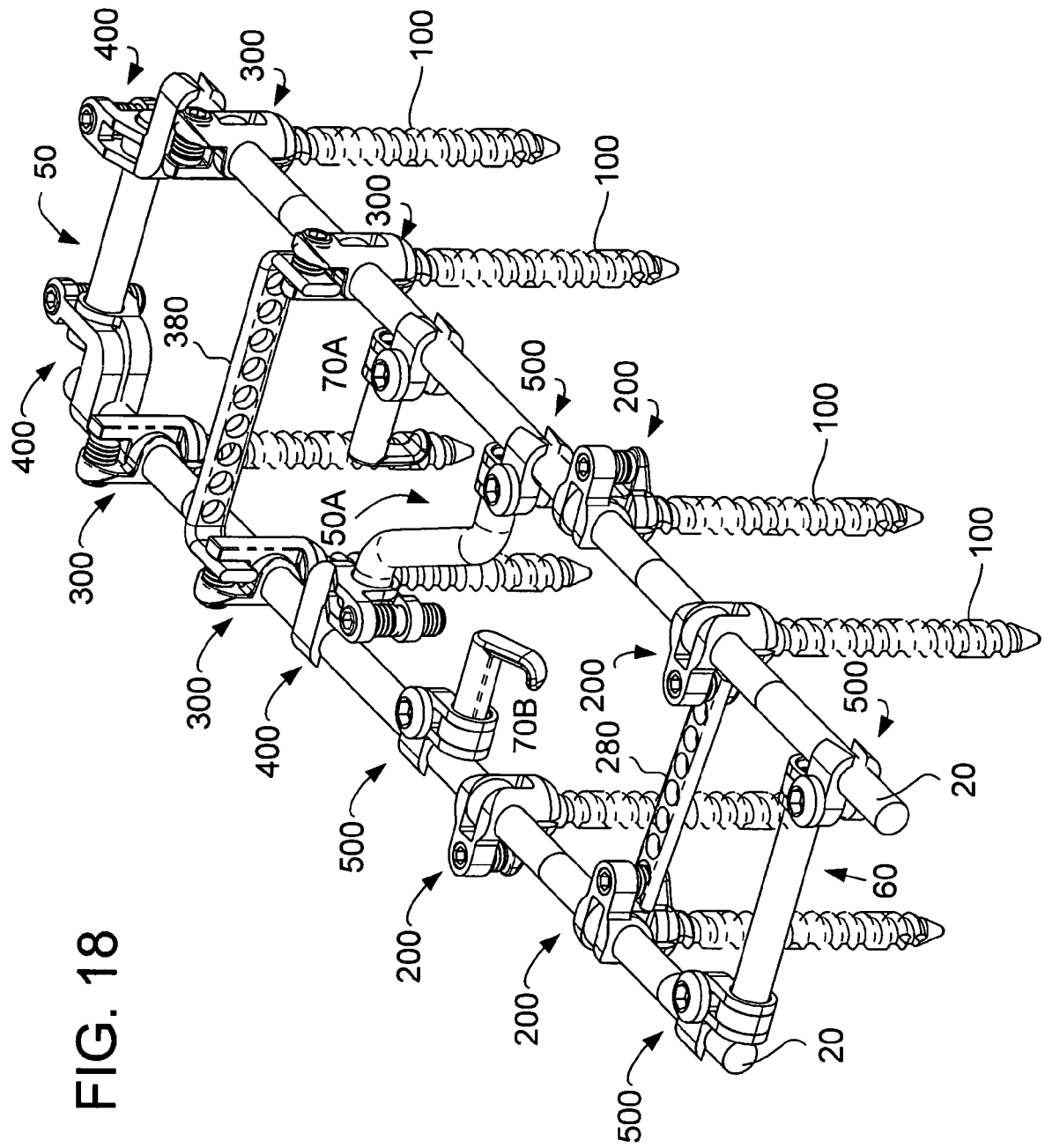

280
282

380
382
384
386

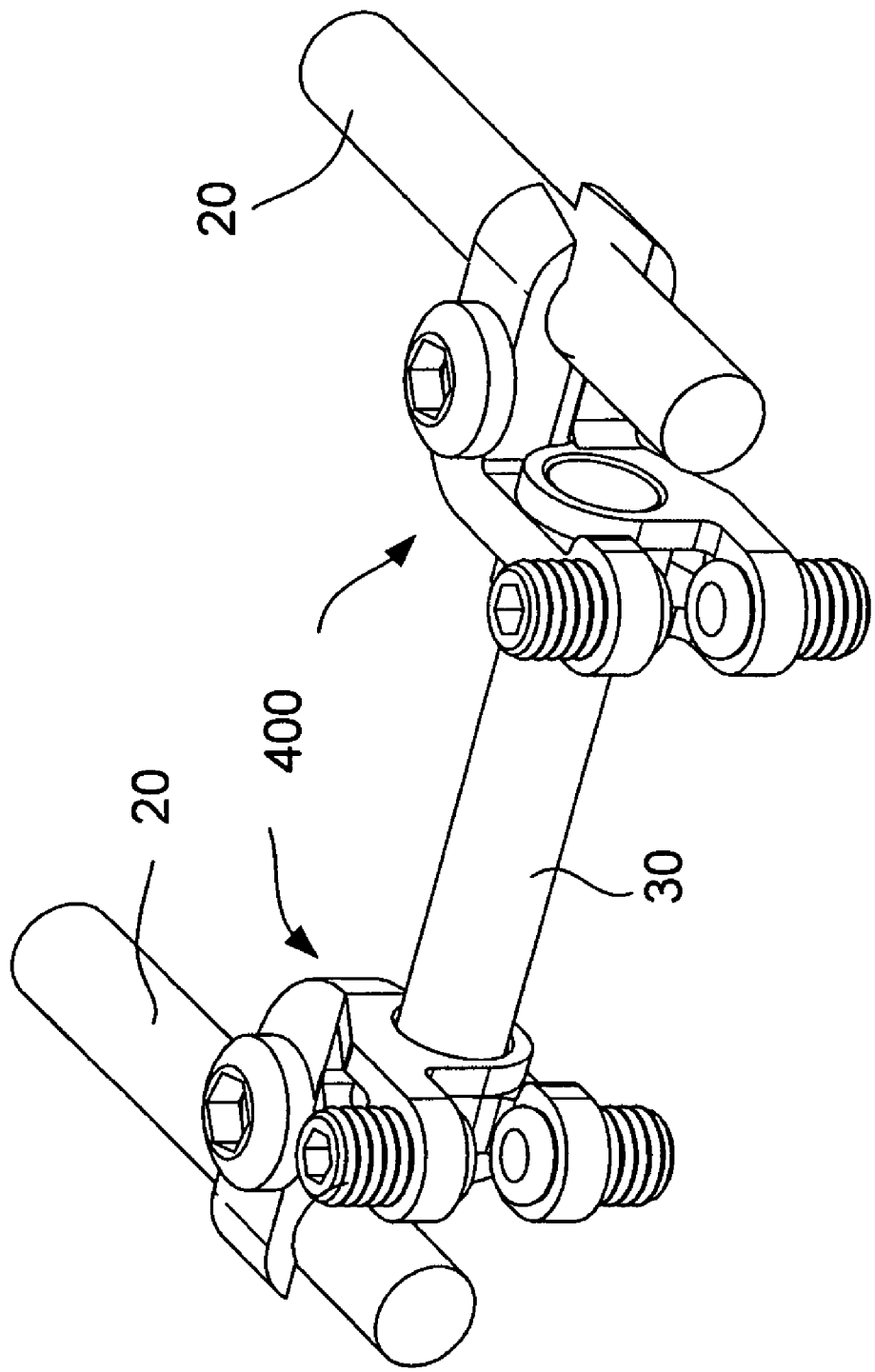

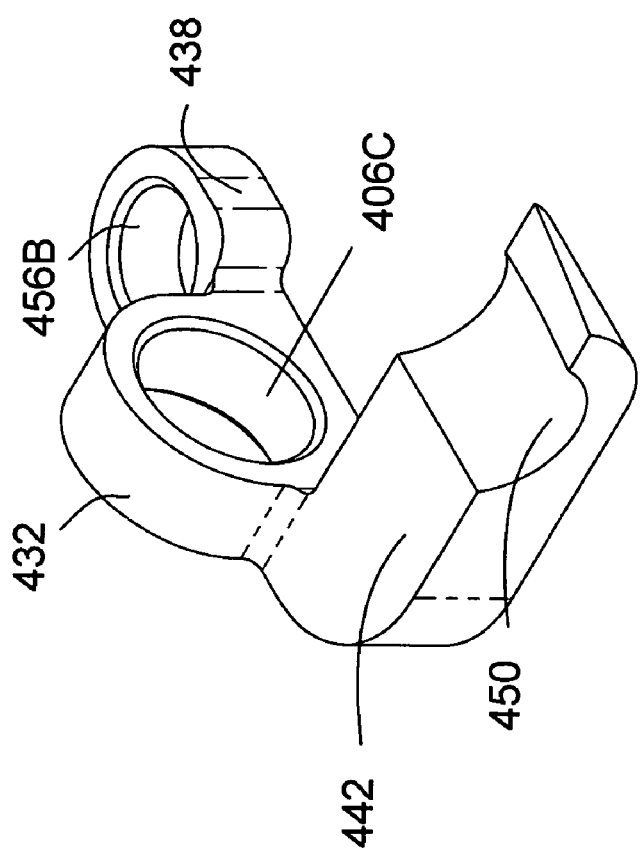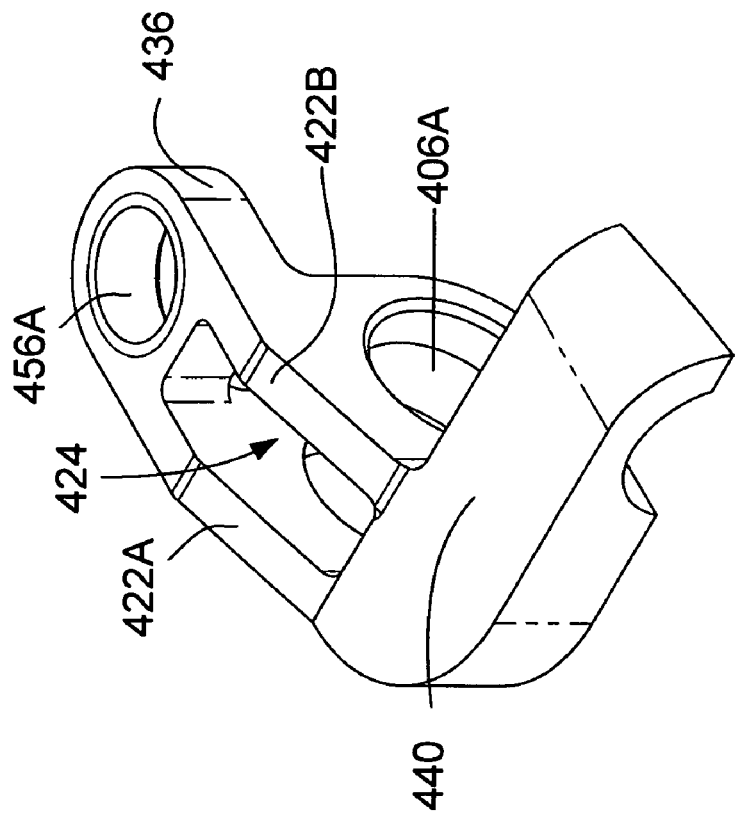

60

500

504

502

558

FIG. 28A
80A
FIG. 28B
80B
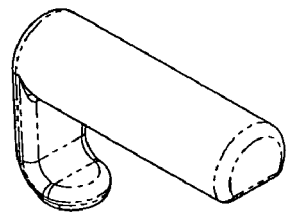
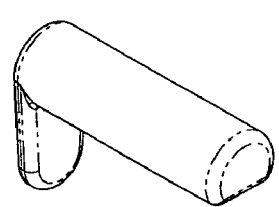
FIG. 29A
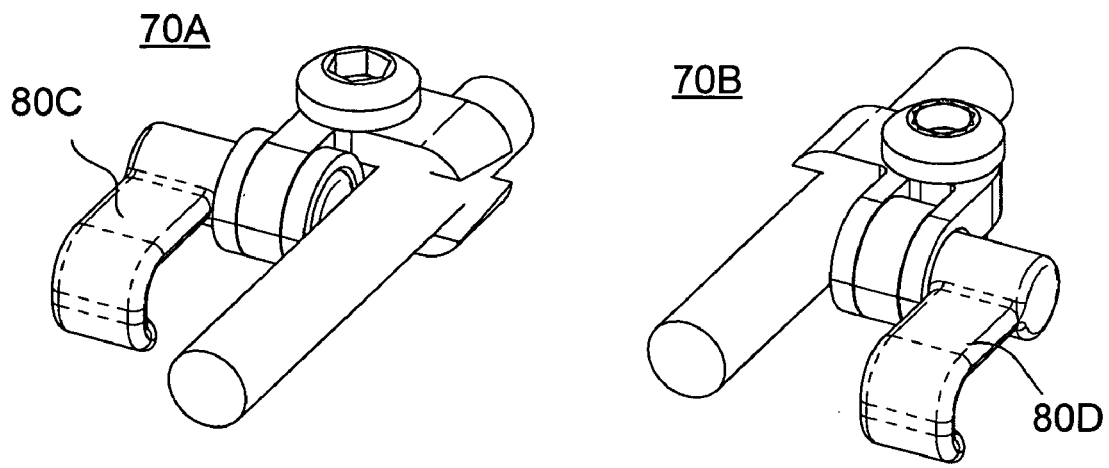
FIG. 29B
80C
FIG. 29C
80D
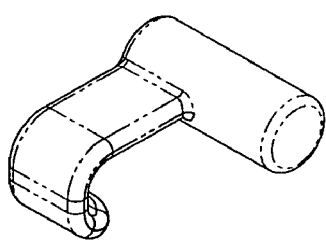
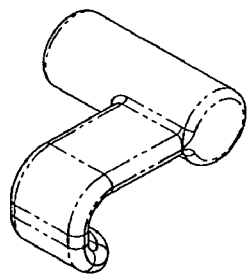

290

SPINAL STABILIZATION USING BONE ANCHOR SEAT AND CROSS COUPLING WITH IMPROVED LOCKING FEATURE

CROSS REFERENCE TO RELATED APPLICATIONS

This application claims the benefit of U.S. Provisional Patent Application No. 60/658,227, filed Mar. 3, 2005, the entire disclosure of which is hereby incorporated by reference.

BACKGROUND OF THE INVENTION

The present invention is directed to vertebral stabilization of a spine using one or more rods anchored onto the vertebrae.

Back pain is one of the most common and often debilitating conditions affecting millions of people in all walks of life. Today, it is estimated that over ten million people in the United States alone suffer from persistent back pain. Approximately half of those suffering from persistent back pain are afflicted with chronic disabling pain, which seriously compromises a person's quality of life and is the second most common cause of worker absenteeism. Further, the cost of treating chronic back pain is very high, even though the majority of sufferers do not receive treatment due to health risks, limited treatment options and inadequate therapeutic results. Thus, chronic back pain has a significantly adverse effect on a person's quality of life, on industrial productivity, and on heath care expenditures.

Degenerative spinal column diseases, such as disc degenerative diseases (DDD), spinal stenosis, spondylolisthesis, and so on, need surgical operation if they do not take a turn for the better by conservative management.

Various methods of spinal immobilization have been known and used during this century in the treatment of spinal instability and displacement. One treatment for spinal stabilization is immobilization of the joint by surgical fusion, or arthrodesis. This method has been known since its development in 1911 by Hibbs and Albee. However, in many cases, and in particular, in cases involving fusion across the lumbosacral articulation and when there are many levels involved, pseudoarthrosis is a problem. It was discovered that immediate immobilization was necessary in order to allow a bony union to form.

Typically, spinal decompression is the first surgical procedure that is performed. The primary purpose of decompression is to reduce pressure in the spinal canal and on nerve roots located therein by removing a certain tissue of the spinal column to reduce or eliminate the pressure and pain caused by the pressure. If the tissue of the spinal column is removed the pain is reduced but the spinal column is weakened. Therefore, fusion surgery (e.g., ALIF, PLIF or posterolateral fusion) is often necessary for spinal stability following the decompression procedure. However, following the surgical procedure, fusion takes additional time to achieve maximum stability and a spinal fixation device is typically used to support the spinal column until a desired level of fusion is achieved. Depending on a patient's particular circumstances and condition, a spinal fixation surgery can sometimes be performed immediately following decompression, without performing the fusion procedure. The fixation surgery is performed in most cases because it provides immediate postoperative stability and, if fusion surgery has also been performed, it provides support of the spine until sufficient fusion and stability has been achieved.

Internal fixation refers to therapeutic methods of stabilization which are wholly internal to the patient. External fixation in contrast involves at least some portion of the stabilization device which is external to the patient's body. Internal fixation is advantageous since the patient is allowed greater freedom with the elimination of the external portion of the device and the possibility of infections, such as pin tract infection, is reduced.

Conventional methods of spinal fixation utilize a rigid spinal fixation device to support an injured spinal part and prevent movement of the injured part. These conventional spinal fixation devices include: fixing screws configured to be inserted into the spinal pedicle or sacral of the backbone to a predetermined depth and angle, rods or plates configured to be positioned adjacent to the injured spinal part, and coupling elements for connecting and coupling the rods or plates to the fixing screws such that the injured spinal part is supported and held in a relatively fixed position by the rods or plates.

A common problem with spinal fixation is the question of how to secure the fixation device to the spine without damaging the spinal cord. The pedicles are a favored area of attachment since they offer an area that is strong enough to hold the fixation device even when the patient suffers from osteoporosis. Since the middle 1950's, methods of fixation have utilized the pedicles. In early methods, screws extended through the facets into the pedicles. Posterior methods of fixation have been developed which utilize wires that extend through the spinal canal and hold a rod against the lamina (such as the Luque system).

U.S. Pat. No. 5,584,831 (the entire disclosure of which is hereby incorporated by reference) discloses a spinal column fixation device 60 that contains a pedicle screw and a clamping apparatus 16 that clamps onto a spherical handle of the screw and receives and interconnecting rod. The clamping apparatus 16 has a cap member 62 with a first end 64 having a generally spherical configuration that forms a cavity 68, which receives the spherical handle 48 of the screw. A second end 66 of the clamping apparatus 16 contains a second cavity 70 for receiving a stabilizing rod 72. The cap member 62 has an aperture 74 that receives a threaded bolting member 76. A base member 82 has a first end 84 having a cavity 88 connected to a segment of the spherical handle end 48. A second end 82 has a cavity 90 for engaging a segment of the stabilizing rod 72. The bolting member 76 and base member 82 cooperate so that the spherical handle end 48 and stabilizing rods are secured together as the bolting member 76 is turned.

Other types of clamping apparatuses for connecting bone screws and interconnecting rods are described in U.S. Patent Application Nos.: 2004/0147929 and 2004/0039385, the entire disclosures of which are hereby incorporated by reference.

Among the problems with the aforementioned systems is that the engagement between the clamping apparatuses and the interconnecting rod is of limited surface area and, therefore, is prone to slippage. Therefore, conventional spinal fixation devices have not provided a satisfactory solution to the problems associated with curing spinal diseases. Additionally, existing fixation devices utilize components that are not proven to provide long-term stability and durability, and are cumbersome and overly complex in terms of how they are adjusted and/or attach to the vertebral bones.

SUMMARY OF THE INVENTION

In accordance with one or more embodiments of the present invention, a stabilization system for implantation in a patient includes: a first pivot element including at least one first aperture, a first engagement element, and a first locking element; a second pivot element including at least one second aperture, a second engagement element, and a second locking element, wherein: the first and second apertures are sized, shaped and disposed in substantial axial alignment such that they are operable to receive the stabilization rod therethrough, and displacement of the first and second locking elements relative to one another urges the first and second apertures to misalign and thereby clamp the stabilization rod.

In one or more embodiments, the first and second engagement elements are operable to engage a head of a bone anchor in response to the displacement of the first and second locking elements relative to one another. Additionally or alternatively, the first and second engagement elements are operable to engage a stabilization member for extension in a transverse direction relative to the stabilization rod in response to the displacement of the first and second locking elements relative to one another. The transverse stabilization member may be a rod of circular (or other) cross-section. Alternatively, the transverse stabilization member may include a stabilization hook.

Other aspects, features, advantages, etc. will become apparent to one skilled in the art when the description of the preferred embodiments of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited to the precise arrangements and instrumentalities shown.

FIG. 11 is a perspective view of a bone stabilizer system in accordance with one or more further embodiments of the present invention;

FIG. 12 is a partial cross-sectional view of the bone stabilizer system of FIG. 11 taken through line 12-12;

FIG. 13 is a perspective view of a portion of a tulip suitable for use with the bone stabilizer system of FIG. 11 and/or one or more other embodiments of the present invention;

FIG. 14 is a top view of the tulip of FIG. 11;

FIG. 15 is a side view of the tulip of FIG. 11;

FIG. 18 is a perspective view of a composite system employing a number of stabilizing systems and elements for coupling longitudinal stabilization rods to the bone(s) of a patient and to interconnect the stabilization rods together or to other structures;

FIG. 20 is a perspective view of a cross-coupling apparatus suitable for use in interconnecting two longitudinal stabilization rods via a transverse stabilization rod;

FIG. 23A is a perspective view of a portion of the transverse rod clamp of FIG. 21;

FIG. 23B is a perspective view of another portion of the transverse rod clamp of FIG. 21;

FIGS. 28A and 28B are perspective views of hooks that may be employed with the transverse rod clamps of FIGS. 21, 25 or other embodiments herein;

FIG. 29A is a perspective view of two transverse stabilization systems that may be employed to couple a longitudinal stabilization rod to another structure using the transverse rod clamps of FIG. 25 (or other embodiments herein) and a further hook design;

FIGS. 29B and 29C are perspective views of the hooks of FIG. 29A;

DETAILED DESCRIPTION

Figure 2:
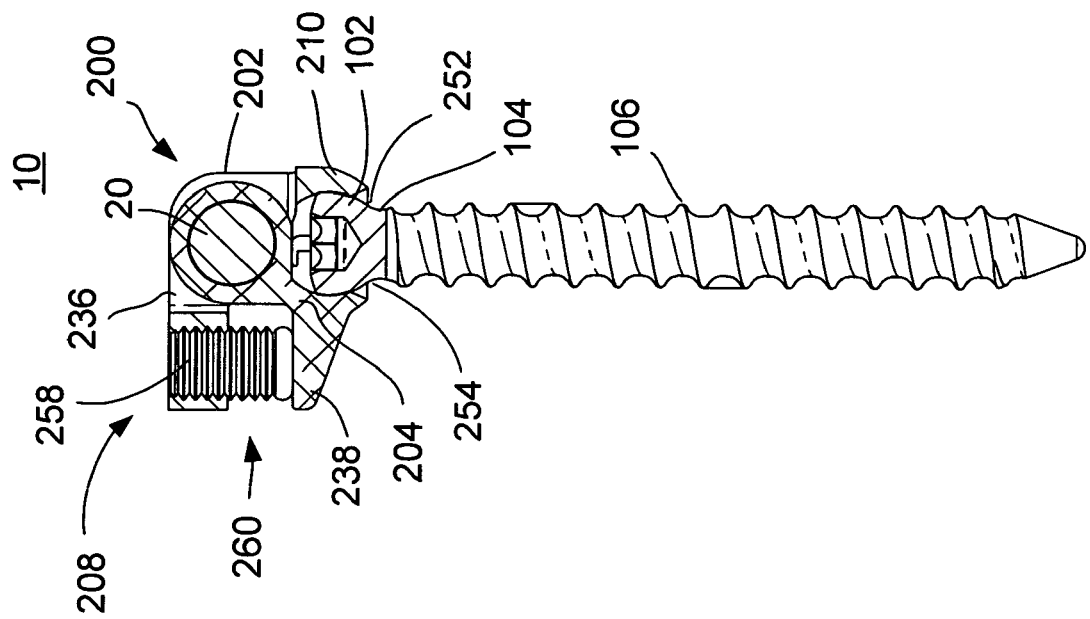
FIG. 2 is a partial cross-sectional view of the bone stabilizer system of FIG. 1 taken through line 2-2.

FIGS. 1-7 illustrate an embodiment of a spinal stabilizer system 10 in accordance with one or more aspects of the present invention. In use, it is understood that a plurality of the stabilizing systems 10 (e.g., pairs thereof) may secure one or more elongate elements, such as one or more stabilization rods (longitudinally oriented and/or cross-rods), cross-link elements, etc., for internal fixation of respective bones of a patient, such as vertebrae of the spine.

The system 10 includes an anchor 100 and an anchor seat (or tulip) 200 that cooperate to fix a portion of an elongate element, such as stabilization rod 20, to a bone. The bone anchor 100 includes a head 102, a neck 104, and a shaft 106, where the neck 104 interconnects the head 102 and the shaft 106. The shaft 106 extends away from the head 102 and is operable for connection to the bone of the patient. For example, the shaft 106 may include threads that may engage a bore made in the bone such that the anchor 100 is secured to the bone of the patient.

The tulip 200 includes a first pivot element 202, and a second pivot element 204 that cooperate to interconnect the stabilization rod 20 to the bone anchor 100. The first and second pivot elements 202, 204 are adapted to produce a passage 206 through which the stabilization rod 20 may slide. Thus, the surgeon may position the tulip 200 along the stabilization rod 20 in a desirable position relative to, among other things, the anatomy of the patient and the position of the bone anchor 100. The tulip 200 also includes a locking mechanism 208 that is operable to manipulate the passage 206 such that it does not permit the stabilization rod 20 to slide within the tulip 200, thereby fixing the tulip 200 with respect to the rod 20. The locking mechanism 208 is also operable to simultaneously cause an anchor engagement mechanism 210 to clamp the head 102 of the bone anchor 100 to fix the tulip 200 thereto.

Figure 1:
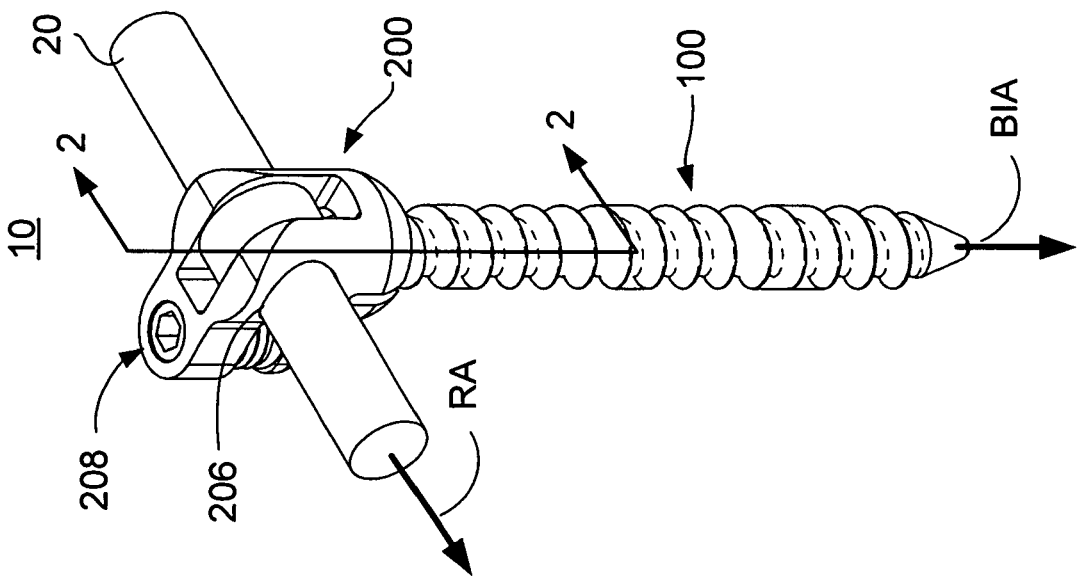
FIG. 1 is a perspective view of a bone stabilizer system in accordance with one or more embodiments of the present invention.
Figure 4:
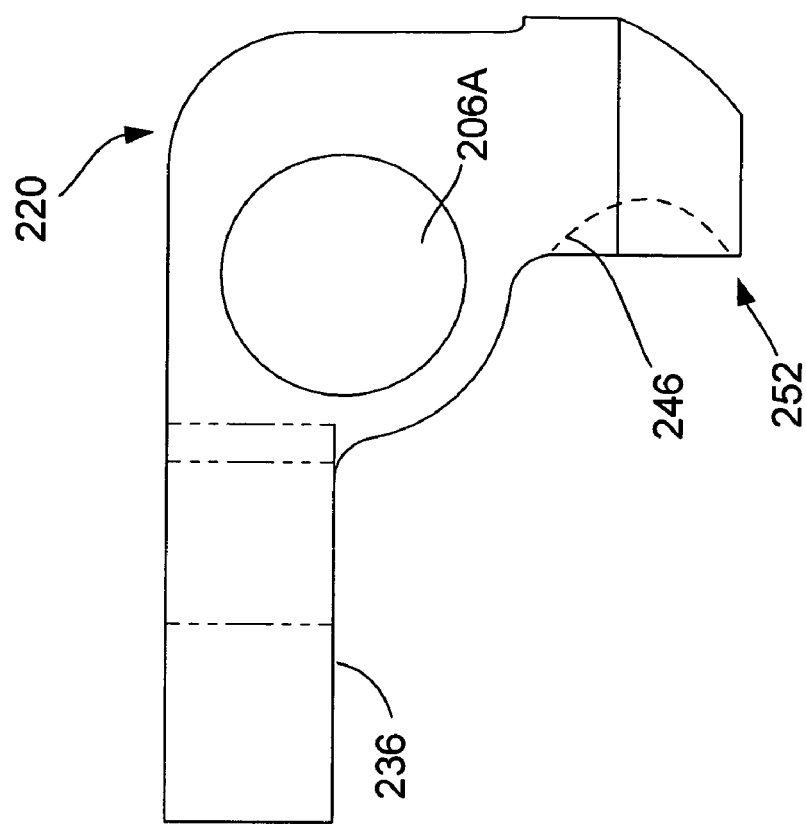
FIG. 4 is a side view of the tulip of FIG. 3.
Figure 3:
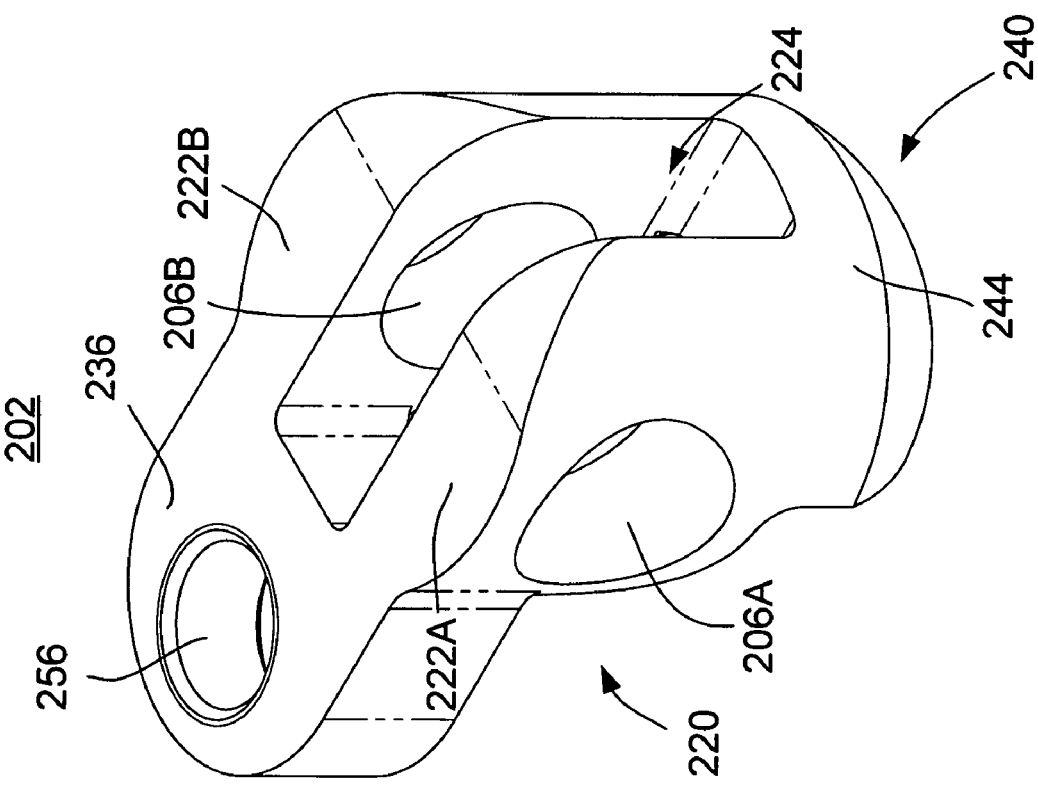
FIG. 3 is a perspective view of a portion of a tulip suitable for use with the bone stabilizer system of FIG. 1 and/or one or more other embodiments of the present invention.
Figure 6:
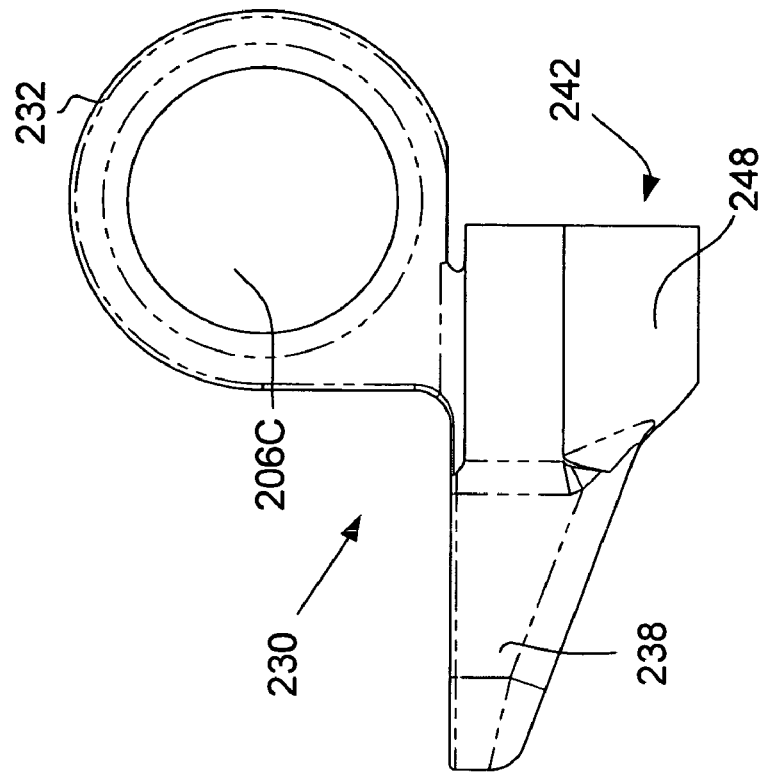
FIG. 6 is a side view of the tulip of FIG. 5.
Figure 5:
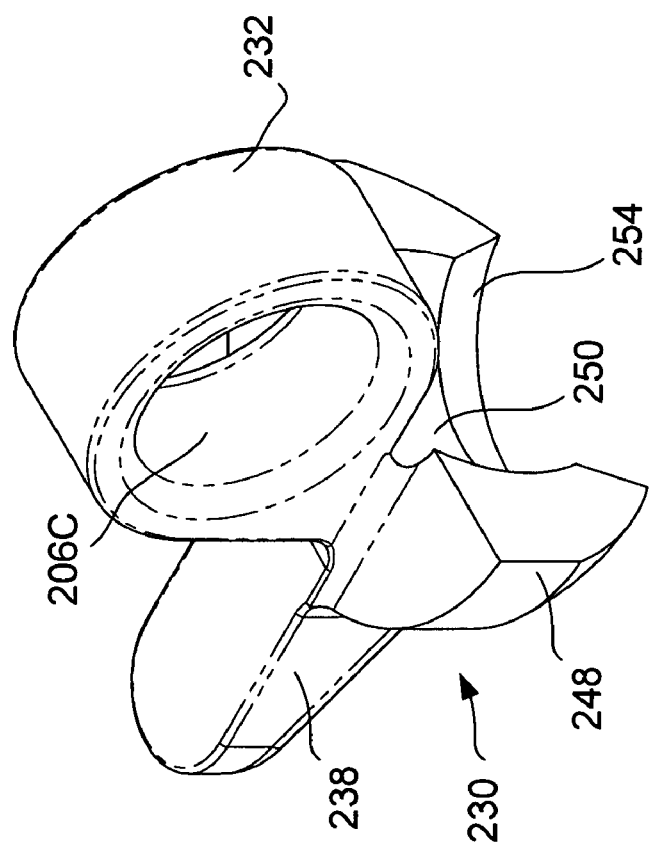
FIG. 5 is a perspective view of another portion of the tulip of FIG. 1 (and/or one or more other embodiments of the present invention)
Figure 7:
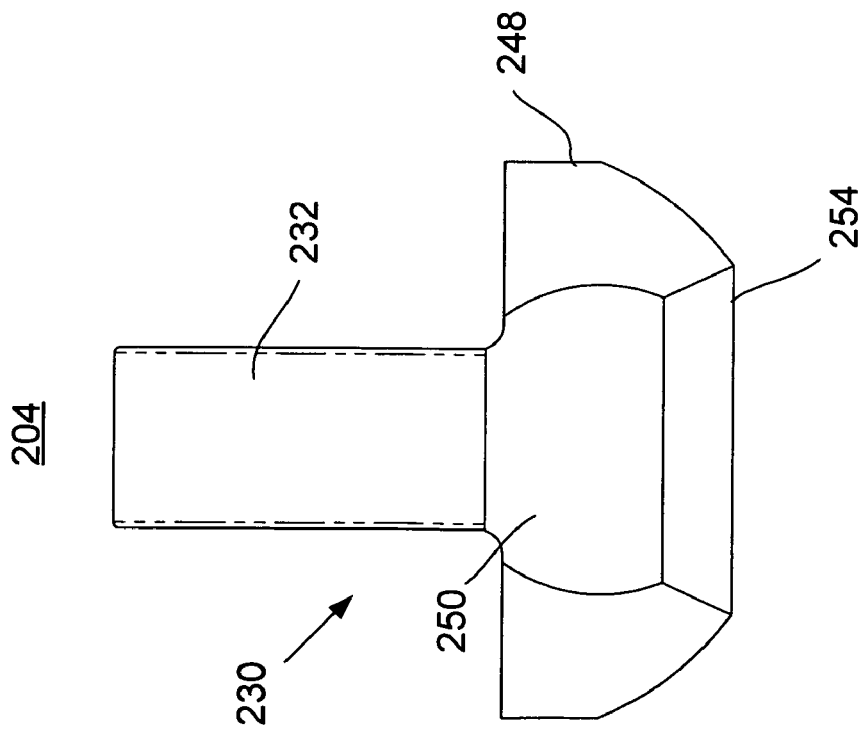
FIG. 7 is a front view of the tulip of FIG. 5.

As best seen in FIGS. 3 and 4, the first pivot element 202 includes a body 220 having wall members 222A, 222B, where each wall member 222A, 222B includes a respective aperture 206A, 206B. The apertures 206A, 206B cooperate to form at least part of the aforementioned passage 206 that receives the stabilization rod 20. In a preferred embodiment, the wall members 222A, 222B are spaced apart such that they define a recess, gap, or space 224 within the body 220. As best seen in FIGS. 5-7, the second pivot element 204 includes a body 230 having at least one wall member, preferably a single wall member 232. The wall member 232 includes an aperture 206C extending therethrough. The wall members 222A, 222B of the first pivot element 202 may be disposed adjacent to the wall member 232 of the second pivot element 204 such that the apertures 206A, 206B, and 206C are in substantial axial alignment and cooperate to form the passage 206 for receiving the stabilization rod 20. As best seen in FIGS. 1 and 2, the wall member 232 of the second pivot element 204 may be disposed in the space 224 of the second pivot element 202 such that the apertures 206A, 206B, and 206C are in substantial axial alignment, with the aperture 206C being located between the apertures 206A and 206B.

Each of the first and second pivot elements 202, 204 preferably include a respective locking element that cooperate to form at least part of the locking mechanism 208. For example, the first and second pivot elements 202, 204 may include respective locking elements 236, 238, which depend from the respective bodies 220, 230. In a preferred embodiment, each of the locking elements 236, 238 act as respective lever arms, which when manipulated urge the respective first and second pivot elements 202, 204 to rotate about the stabilization rod 20 (when it is in the passage 206), in particular about a rod axis RA. (The apertures 206A, 206B, and 206C of the passage 206 define the rod axis RA, which is axially aligned with a central axis of stabilization rod 20 disposed within the apertures.) In one or more embodiments, the displacement of the first and second locking elements 236, 238 relative to one another (e.g., away from one another) urges the apertures 206A, 206B to misalign with respect to the aperture 206C, thereby clamping the stabilization rod 20. In particular, the displacement of the lever arms 236, 238 away from one another causes the wall members 222A, 222B of the first pivot element 202 to tend to rotate with respect to the wall member 232 of the second pivot element 204 about the rod axis RA.

The tendency for the wall members 222A, 222B, and 232 to rotate also causes the bodies 220, 230 of the respective pivot elements 202, 204 to engage and lock the head 102 of the bone anchor 100. More particularly, each of the bodies 220, 230 includes a respective anchor engagement element 240, 242. The anchor engagement element 240 of the body 220 includes an outer surface 244 and an inner surface 246, where the inner surface 246 has a contour that is operable to engage at least a portion of the head 102 of the bone anchor 100. The contour of the inner surface 246 is generally curved in one or more embodiments to complement a generally curved contour of the head 102. Similarly, the anchor engagement element 242 of the pivot element 204 includes an outer surface 248 and an inner surface 250, where the inner surface includes a contour that is operable to engage another portion of the head 102 of the bone anchor 100. The contours of the inner surfaces 246 and 250 may define a contour that is fully or semi-spherical, cylindrical, etc.

The aforementioned displacement of the lever arms 236, 238 away from one another and resultant pivoting of the elements 202, 204 about the rod axis RA causes a corresponding movement of the respective anchor engagement elements 240, 242 toward one another. Thus, the inner surfaces 246, 250 of the respective anchor engagement elements 240, 242 are generally directed toward one another and engage opposite sides of the head 102. It is noted that the inner surfaces 246, 250 of the anchor engagement elements 240, 242 define an inner volume to receive the head 102 of the bone anchor 100 to achieve various articulations of the tulip 200 about the head 102. Displacement of the lever arms 236, 238, however, causes the volume to collapse and the inner surface 246, 250 to engage the head 102 to fix the position of the tulip 200 with respect to the bone anchor 100.

The inner surface 246 of the anchor engagement element 240 terminates at an edge 252, while the inner surface 250 of the anchor engagement element 242 terminates at an edge 254. The respective edges 252, 254 define an aperture through which the bone anchor 100, e.g., the neck 104 thereof, may extend out of the volume and away from the tulip 200.

The clamping engagement of the inner surfaces 246, 250 against the head 102 of the bone anchor 100 causes a reactive force tending to oppose the rotation of the wall members 222A, 222B, and 232 about the rod axis RA, and oppose the displacement of the lever arms 236, 238 away from one another. As a consequence, the wall members 222A, 222B, and 232 will be urged to misalign as the wall member 232 is urged out of the space 224. This tendency toward misalignment clamps the stabilization rod 20 within the passage 206.

The locking mechanism 208 may include a bore 256 extending through at least one of the lever arms 236, 238. In the embodiment illustrated, the bore 256 is disposed in the lever arm 236 of the first pivot element 202. In a preferred embodiment, the bore 256 is threaded and extends toward the lever arm 238. The locking mechanism 208 also includes a locking element 258 that is operable to engage the bore 256 and cause the displacement of the lever arms 236, 238 away from one another. For example, the locking element 258 may include a threaded shaft having proximal and distal ends, where the distal end directly or indirectly engages the lever arm 238 to push the lever arm 238 away form the lever arm 236 in response to turning the threaded shaft through the bore 256. As best seen in FIG. 2, the lever arms 236, 238 may be spaced apart and define a gap 260 therebetween. In this embodiment, the locking element 258, which is a threaded shaft, such as a set screw, extends through the bore 256, across the gap 260 and directly engages the lever arm 238.

Figure 8:
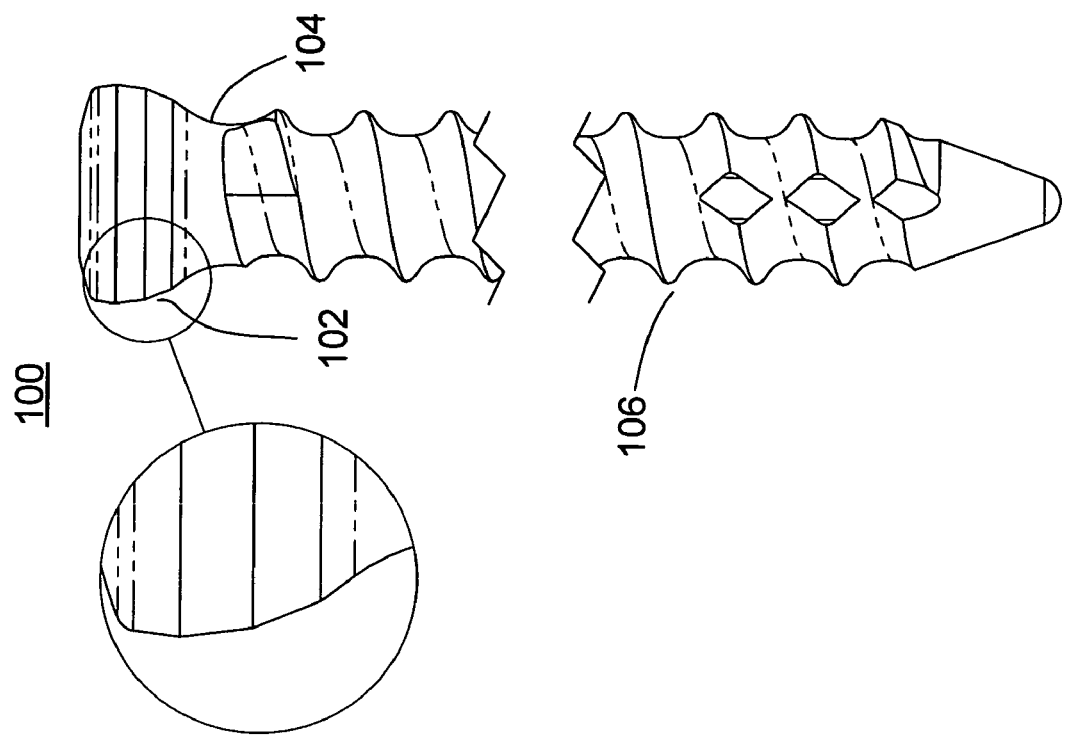
FIG. 8 is a side view of a bone anchor (a screw) suitable for use with the bone stabilizer system of FIG. 1 and/or one or more other embodiments of the present invention.

With reference to FIG. 8, the head 102 of the bone anchor 100 may include a friction enhancement feature. The friction enhancement feature is preferably operable to facilitate fixed orientation between the tulip 200 and the bone anchor 100 by increasing the stability of the engagement between the head 102 and the inner surface 246, 250 of the anchor engagement elements 240, 242. By way of example, the friction enhancement feature may include at least one of ridges, grooves, protrusions, dimples, crosshatching, knurling, etc.

As noted above, the apertures 206A, 206B, and 206C of the passage 206 define the rod axis (RA), which is axially aligned with a central axis of stabilization rod 20 disposed within the apertures. The rod axis RA is generally transverse to the bone insertion axis BIA. In the embodiment of FIGS. 1-7, the lever arms 236, 238 extend from the respective bodies 220, 230 transversely with respect to both the rod axis RA and the bone insertion axis BIA. In one or more embodiments, the lever arms 236, 238 may extend substantially perpendicularly from the bodies 220, 230, respectively.

Figure 10:
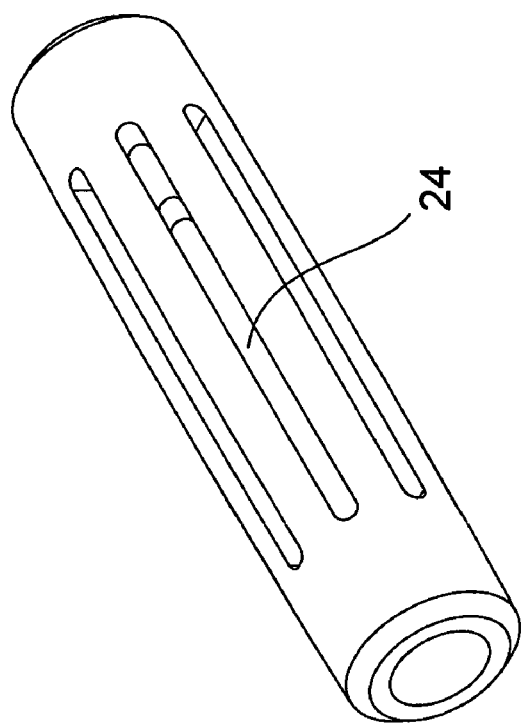
FIG. 10 is a perspective view of an insert for use in pre-assembling the tulip of FIG. 1 (and/or one or more other embodiments of the present invention)
Figure 9:
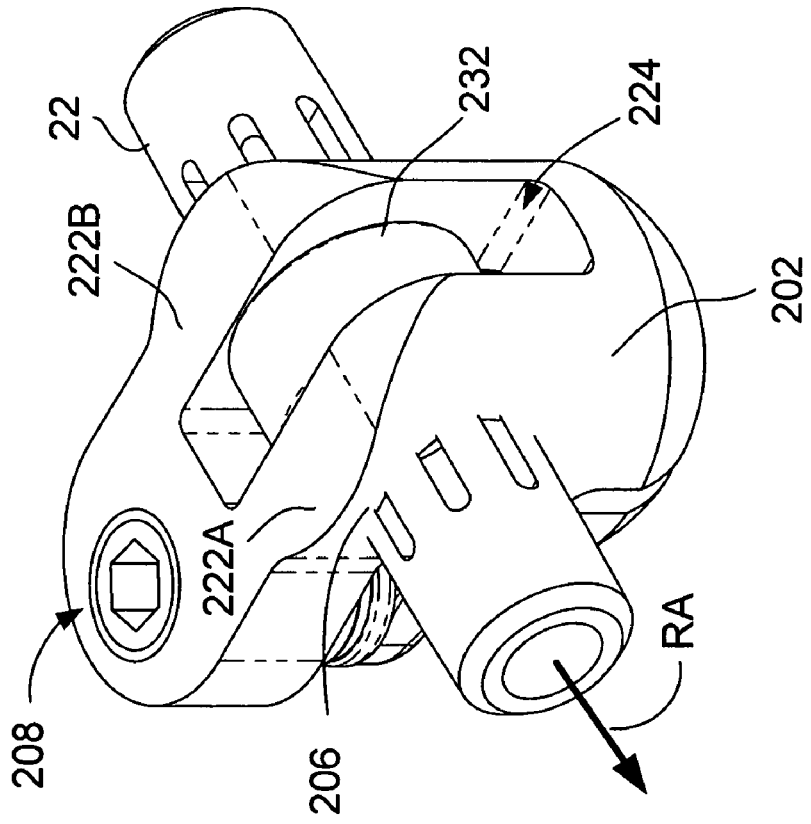
FIG. 9 is a perspective view of the tulip of FIG. 1 (and/or one or more other embodiments of the present invention) in a pre-assembled form using an insert.

Reference is now made to FIGS. 9 and 10, where FIG. 9 is a perspective view of the tulip 200 as a pre-assembly for use by a surgeon during an implant procedure. The surgeon is preferably provided with the tulip 200 having an insert 22 placed in the passage 206. As best seen in FIG. 10, the insert 22 is a generally elongate cylinder roughly approximating the diameter of the stabilization rod 20 that is to be received in the passage 206. In a preferred embodiment, the insert 22 includes a plurality of slits 24 that permit the insert 22 to have a degree of resiliency in its diameter so that it may be readily slid into, and out of, the passage 206 prior to and during the implantation surgery, without falling out on its own accord. The insert 22 is preferably provided in the passage 206 prior to implantation in order to keep the respective pivot elements 202, 204 from becoming disengaged, thereby providing the surgeon with a pre-assembled tulip 200 ready for implantation.

Thus, in accordance with an exemplary surgical protocol, the surgeon may bore a hole in the bone of the patient, drive the bone anchor 100 into the hole, and then select the tulip 200 (for example, from among a plurality of different sizes and styles suitable for use in connection with the particular bone anchor 100 and/or the particular anatomy of the patient). The surgeon may then size the stabilization rod 20, for example, by selecting from among a plurality of pre-cut lengths of rod, or cutting the rod 20 during the surgical procedure to a desired length. Next, the surgeon may align the stabilization rod 20 with the insert 22 and press the stabilization rod against one of the ends of the insert 22 to push the insert through the passage 206 and, at the same time, insert the stabilization rod 20 into the passage 206 such that the insert is disengaged from the tulip 200. At this point, the respective pivot elements 202, 204 remain engaged vis-à-vis the stabilization rod 20 being received in the passage 206.

Next, the surgeon may loosen the locking mechanism 208 such that the anchor engagement elements 240, 242 spread apart and permit reception of the head 102 within the volume. Next, the surgeon may tighten the locking mechanism 208, for example, by driving the locking element 258 through the bore 256 such that the distal end thereof engages the lever arm 238 and displaces the lever arms 236, 238 away from one another. As discussed above, such displacement forces the respective anchor engagement elements 240, 242 toward one another such that the inner surfaces 246, 250 engage the head 102 and lock the tulip 200 to the bone anchor 100. Concurrently, the engagement of the inner surfaces 246, 250, against the head 102 of the bone anchor 100 causes the reactive force to oppose the rotation of the wall members 222A, 222B and 232 about the rod axis RA and oppose the displacement of the lever arms 236, 238 away from one another. Consequently, the wall members 222A, 222B, and 232 will be urged to misalign and thereby clamp the stabilization rod 20 within the passage 206. The resultant situation is that the tulip 200 is fixed in position with respect to the bone anchor 100 and with respect to the stabilization rod 20.

Reference is now made to FIGS. 11-17, which illustrate one or more further embodiments of the present invention. FIG. 11 is a perspective view of an alternative stabilizing system 10A that may be utilized to secure a stabilization rod 20 to the bone anchor 100 utilizing a tulip 300 having an alternative design. The tulip 300 shares some similar features with respect to the tulip 200 discussed hereinabove with respect to FIGS. 1-7. The tulip 300, however, also includes one or more additional features which will be discussed hereinbelow.

The tulip 300 includes a first pivot element 302, and a second pivot element 304 that cooperate to interconnect the stabilization rod 20 to the bone anchor 100. The first and second pivot elements 302, 304 are adapted to produce a passage 306 through which the stabilization rod 20 may slide. Thus, as with the tulip 200, the surgeon may position the tulip 300 along the stabilization rod 20 and then manipulate the passage 306 (via the locking mechanism 308) such that it does not permit the stabilization rod 20 to slide within the tulip 300, thereby fixing the tulip 300 with respect to the rod 20. The locking mechanism 308 is also operable to simultaneously cause the anchor engagement mechanism 310 to clamp the head 102 of the bone anchor 100 to fix the tulip 300 thereto.

As with the tulip 200, the first pivot element 302 includes a body 320 having wall members 322A, 322B that are spaced apart such that they define a recess, gap, or space 324 within the body 320. The second pivot element 304 also includes a body 330, preferably having a single wall member 332. The wall member 332 of the second pivot element 304 is disposed in the space 324 of the second pivot element 302 such that the apertures 306A, 306B, and 306C are in substantial axial alignment and cooperate to form the passage 306 for receiving the stabilization rod 20.

The locking mechanism 308 includes respective locking elements 336, 338, which depend from the respective bodies 320, 330 of the first and second pivot elements 302, 304. Each of the locking elements 336, 338 preferably act as respective lever arms, which when manipulated urge the respective first and second pivot elements 302, 304 to rotate about the stabilization rod 20 and about the rod axis RA. (The apertures 306A, 306B, and 306C of the passage 306 define the rod axis RA.) The displacement of the first and second locking elements 336, 338 relative to one another (e.g., away from one another) causes the bodies 320, 330 of the respective pivot elements 302, 304 to move toward one another such that the inner surfaces 346, 350 of the respective anchor engagement elements 340, 342 engage opposite sides of the head 102. The clamping engagement of the inner surfaces 346, 350 against the head 102 of the bone anchor 100 causes a reactive force tending to oppose the rotation of the wall members 322A, 322B, and 332 about the rod axis RA, and oppose the displacement of the lever arms 336, 338 away from one another. As a consequence, the wall members 322A, 322B, and 332 will be urged to misalign, as the wall member 332 is urged out of the space 324, and clamp the stabilization rod 20 within the passage 306.

The rod axis (RA) is axially aligned with a central axis of stabilization rod 20 disposed within the apertures. As with the tulip 200, the rod axis RA of the tulip 300 is generally transverse to the bone insertion axis BIA and the lever arms 336, 338 extend from the respective bodies 320, 330 transversely with respect to the rod axis RA. The lever arms 336, 338 of the tulip 300, however, extend from the respective bodies 320, 330 substantially parallel to the bone insertion axis BIA.

Figure 17:
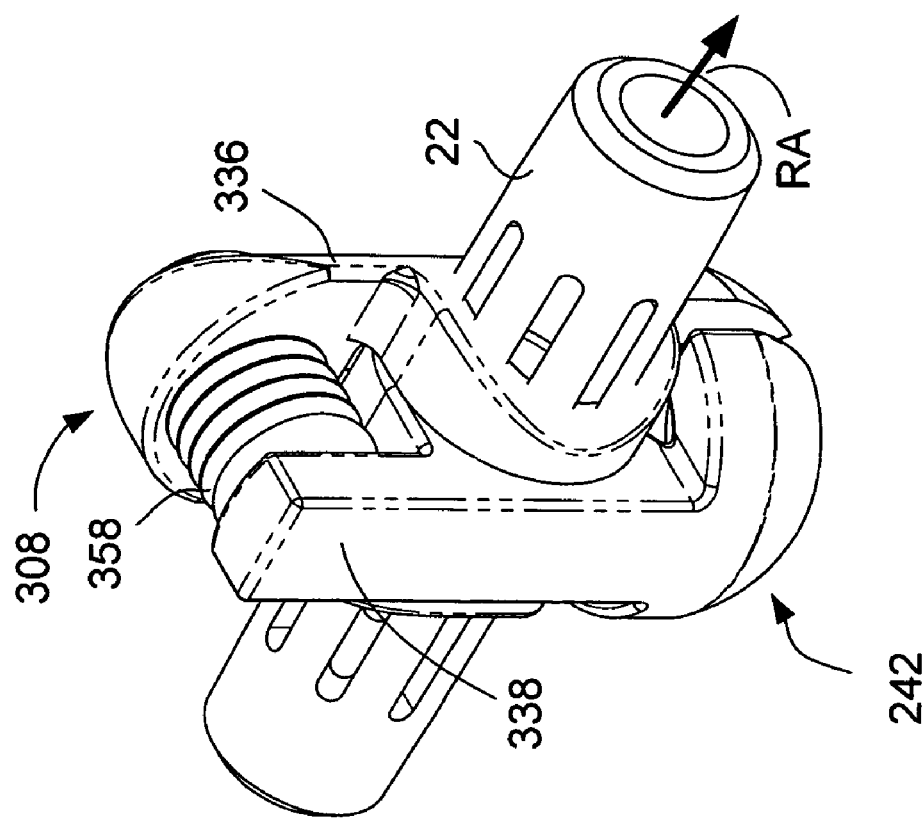
FIG. 17 is a perspective view of the tulip of FIG. 11 in a pre-assembled form using an insert.
Figure 16:
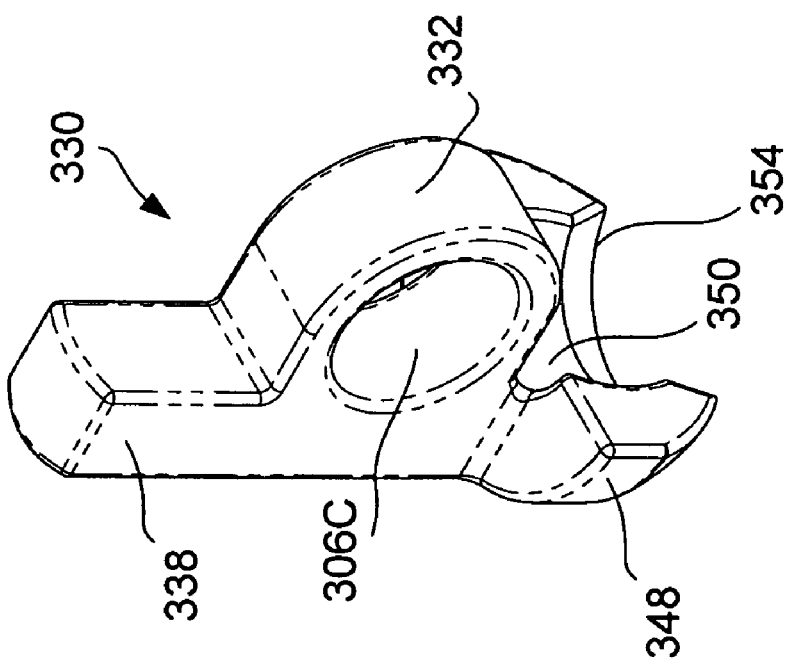
FIG. 16 is a perspective view of another portion of the tulip of FIG. 11 (and/or one or more other embodiments of the present invention)

As illustrated in FIG. 17, the tulip 300 may be provided as a pre-assembly for use by a surgeon by placing the insert 22 in the passage 306 in order to keep the respective pivot elements 302, 304 from becoming disengaged.

Reference is now made to FIG. 18, which is a perspective view of a number of stabilization systems coupled to a pair of stabilization rods 20. Those skilled in the art will recognize that the number of bone anchors, tulips and other stabilization mechanisms coupled to the rods 20 are not likely to be used in the configuration shown. FIG. 18 does, however, provide an indication of some of the many configurations achievable using various embodiments of the invention. For example, the rods 20 may be coupled to one or more bones of the patient using the stabilization system 10 (in which a pair of bone anchors 100 are connected to the rods 20 by way of the tulips 200). Alternatively, the rods 20 may be coupled to one or more bones of the patient using the stabilization system 10A (in which a pair of bone anchors 100 are connected to the rods 20 by way of the tulips 300).

Figure 19A:
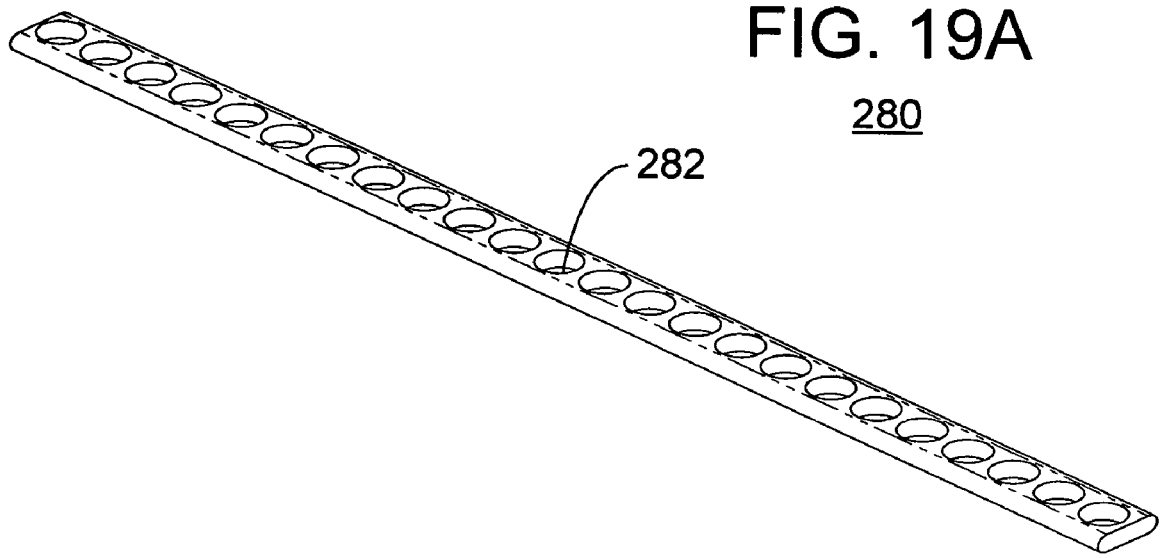
FIG. 19A is a perspective view of a cross-link member suitable for use in interconnecting two tulips, such as the tulip of FIG. 1.

In an alternative embodiment, the stabilization system 10 may include a cross-link member 280 that extends transversely from, and connects, each of the tulips 200. As seen in FIGS. 18 and 19A, the cross-link member 280 is of generally elongate construction having first and second ends. Recalling from the discussion above that the first and second lever arms 236, 238 are spaced apart defining a gap 260 therebetween, the ends of the cross-link member 280 are positioned in the respective gaps 260 of the tulips 200. The locking element 258 is operable to engage the cross-link member 280 and directly or indirectly bias it against the second lever arm to: (i) fix the cross-link member 280 to the tulip 200, and (ii) cause the displacement of the first and second lever arms 236, 238. The cross-link member 280 may include one or more apertures 282 therethrough sized and shaped to engage locking element 258.

Figure 19B:
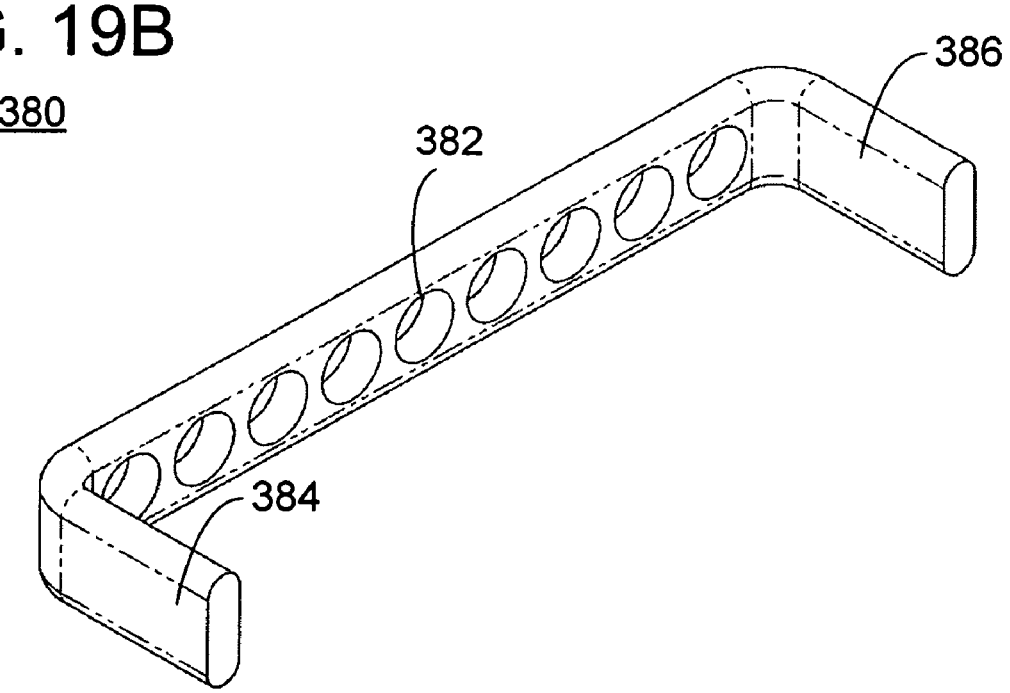
FIG. 19B is a perspective view of an alternative cross-link member suitable for use in interconnecting two tulips, such as the tulip of FIG. 11.

In a further alternative embodiment, the stabilization system 10A may include a cross-link member 380 that extends transversely from, and connects, each of the tulips 300. As seen in FIGS. 18 and 19B, the cross-link member 380 is of generally elongate construction having one or more apertures 382, and first and second transversely extending ends 384, 386. As the lever arms 336, 338 of the tulip 300 extend from the respective bodies 320, 330 substantially parallel to the bone insertion axis BIA, the gaps 360 are presented in such a way that the transversely extending ends 384, 386 may be received in the gaps 360 and permit the cross-link member 380 to extend across the space between the stabilization rods 20. The locking element 358 is operable to engage the cross-link member 380 and directly or indirectly bias it against the second lever arm to: (i) fix the cross-link member 380 to the tulip 300, and (ii) cause the displacement of the first and second lever arms 336, 338.

Turning again to FIG. 18, the stabilization rods 20 may also be coupled to one another by way of a cross coupling apparatus 50. The cross coupling apparatus 50 is shown in another perspective view in FIG. 20. The cross coupling apparatus 50 permits a cross connection between the stabilization rods 20 before or after they are fixed to the bone anchors 100. In this embodiment, the cross coupling apparatus 50 includes a pair of transverse rod clamps 400 and a transverse rod 30.

Figure 21:
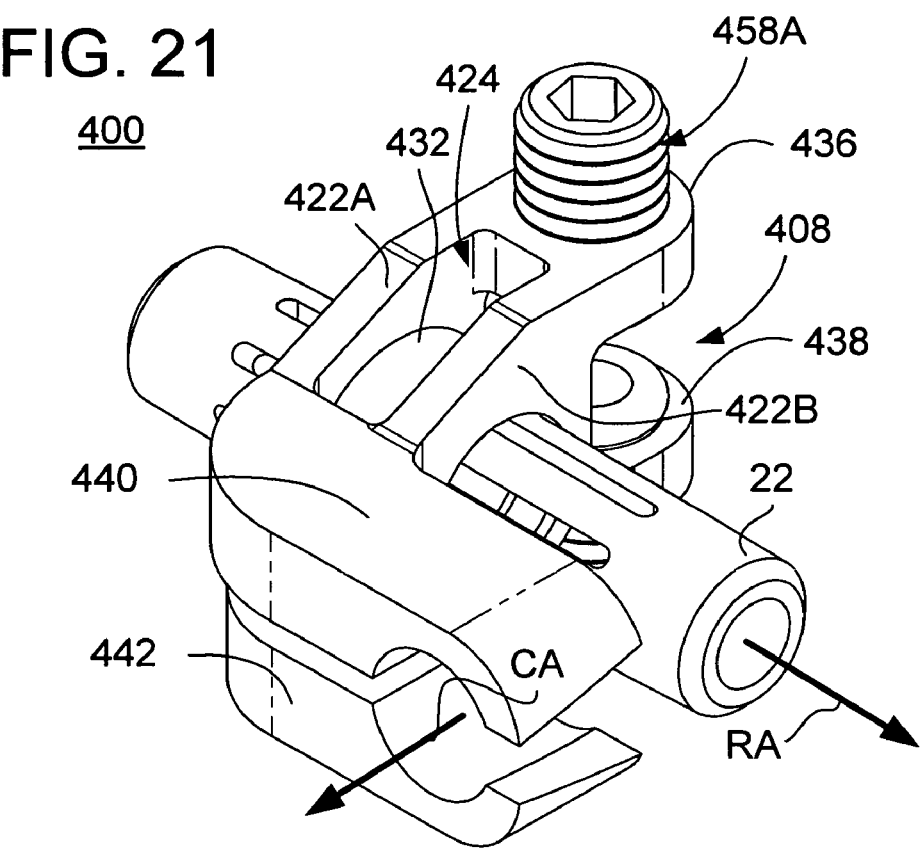
FIG. 21 is a perspective view of a transverse rod clamp of the cross-coupling apparatus of FIG. 20.
Figure 22:
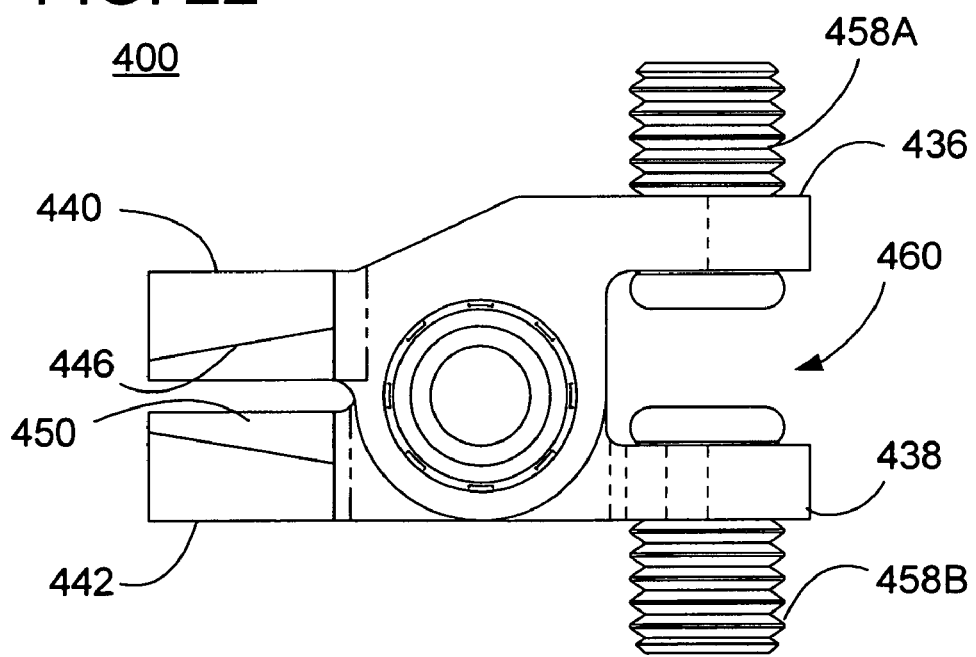
FIG. 22 is a side view of the transverse rod clamp of FIG. 21.

As illustrated in FIGS. 21, 22, and 23A-23B, the transverse rod clamps 400 share some similar features with respect to the tulips 200, 300 discussed hereinabove. As the transverse rod clamps 400 are adapted for coupling the longitudinal stabilization rods 20 and the transverse rod 30 together, however, they also include one or more additional features which will be discussed hereinbelow. As illustrated in FIG. 21, the transverse rod clamp 400 may be provided as a pre-assembly for use by a surgeon by placing the insert 22 in the passage 406 in order to keep the components of the clamp 50 from becoming disengaged.

The transverse rod clamp 400 includes a first pivot element 402, and a second pivot element 404 that cooperate to interconnect the longitudinal stabilization rod 20 to the transverse stabilization rod 30. The pivot elements 402, 404 are adapted to produce a passage 406 through which the transverse stabilization rod 30 may slide. Thus, as with the tulips 200 and 300, the surgeon may position the transverse rod clamp 400 along the transverse stabilization rod 30 and then manipulate the passage 406 (via the locking mechanism 408) such that it does not permit the transverse stabilization rod 30 to slide within the transverse rod clamp 400, thereby fixing the transverse rod clamp 400 with respect to the rod 30. The locking mechanism 408 is also operable to simultaneously cause a rod engagement mechanism 410 to clamp to the longitudinal stabilization rod 20 to fix the transverse rod clamp 400 thereto.

As with the tulips 200 and 300, the first pivot element 402 includes a body 420 having wall members 422A, 422B that are spaced apart such that they define a recess, gap, or space 424 within the body 420. The second pivot element 404 also includes a body 430, preferably having a single wall member 432. The wall member 432 of the second pivot element 404 is disposed in the space 424 of the second pivot element 402 such that the apertures 406A, 406B, and 406C are in substantial axial alignment and cooperate to form the passage 406 for receiving the transverse stabilization rod 30.

The rod axis RA is axially aligned with a central axis of transverse stabilization rod 30 disposed within the apertures. The rod axis RA of the transverse rod clamp 400 is generally transverse to the central axis CA of the longitudinal stabilization rod 20.

The locking mechanism 408 includes respective locking elements 436, 438, which depend from the respective bodies 420, 430 of the pivot elements 402, 404. Each of the locking elements 436, 438 preferably act as respective lever arms, which when manipulated urge the respective pivot elements 402, 404 to rotate about the transverse stabilization rod 30 and about the rod axis RA.

The lever arms 436, 438 extend from the respective bodies 420, 430 transversely with respect to the rod axis RA and substantially parallel to the central axis CA of the longitudinal stabilization rod 20. As best seen in FIG. 21, the lever arms 436, 438 are disposed on an opposite side of the respective wall members 422A, 422B, and 432 (and on an opposite side of the rod axis RA) from the respective rod engagement elements 440, 442. The rod engagement elements 440, 442 extend from the respective bodies 420, 430 such that the central axis CA is laterally offset from the apertures 406A, 406B, 406C, in a direction substantially parallel with the transverse rod axis RA.

The displacement of the locking elements 436, 438 relative to one another (e.g., away from one another) causes the bodies 420, 430 of the respective pivot elements 402, 404 to move toward one another (pivoting about the rod axis RA) such that inner surfaces 446, 450 of the respective rod engagement elements 440, 442 engage opposite sides of the longitudinal stabilization rod 20. The clamping engagement of the inner surfaces 446, 450 against the longitudinal stabilization rod 20 causes a reactive force tending to oppose the rotation of the wall members 422A, 422B, and 432 about the rod axis RA, and oppose the displacement of the lever arms 436, 438 away from one another. As a consequence, the wall members 422A, 422B, and 432 will be urged to misalign, as the wall member 432 is urged out of the space 424, and clamp the transverse stabilization rod 30 within the passage 406.

The locking mechanism 408 may include at least one bore 456 extending through at least one of the lever arms 436, 438. In this embodiment, each of the lever arms 436, 438 include a bore 456A, 456B, respectively, extending therethrough towards the other lever arm.

In a preferred embodiment, the bores 456A, 456B are each threaded and the locking mechanism 208 also includes a respective locking element 458A, 458B that are operable to engage the respective 456A, 456B. The locking elements 458A, 458B are operable to cause the displacement of the lever arms 436, 438 away from one another. For example, the locking elements 458A, 458B may each include a threaded shaft having proximal and distal ends, where the distal end directly or indirectly engages the opposite lever arm to push the lever arms 436, 438 away from one another in response to turning one or both of the threaded shafts through the respective bores 456A, 456B. In a preferred embodiment, the bores 456A, 456B and locking elements 458A, 458B are disposed in axial alignment such that the distal ends of the locking elements 458A, 458B engage one another when one or both of the threaded shafts are turned through the respective bores 456A, 456B.

Among the advantages of having a pair of locking elements 458A, 458B available to the surgeon is that the transverse rod clamp 400 may be used to engage either of the longitudinal stabilization rods 20 and still present one of the locking elements 458A, 458B at least partially toward the surgeon. As such, the locking elements 458A, 458B are operable alone, or in combination, to cause the displacement of the lever arms 436, 438 away from one another by direct or indirect engagement.

Turning again to FIG. 18, an alternative design of a cross coupling apparatus 50A may include a transverse rod 30 having re-entrant bends so that the apparatus may traverse, for example, certain anatomical structures of the patient or other pieces of the stabilization system.

Figure 24:
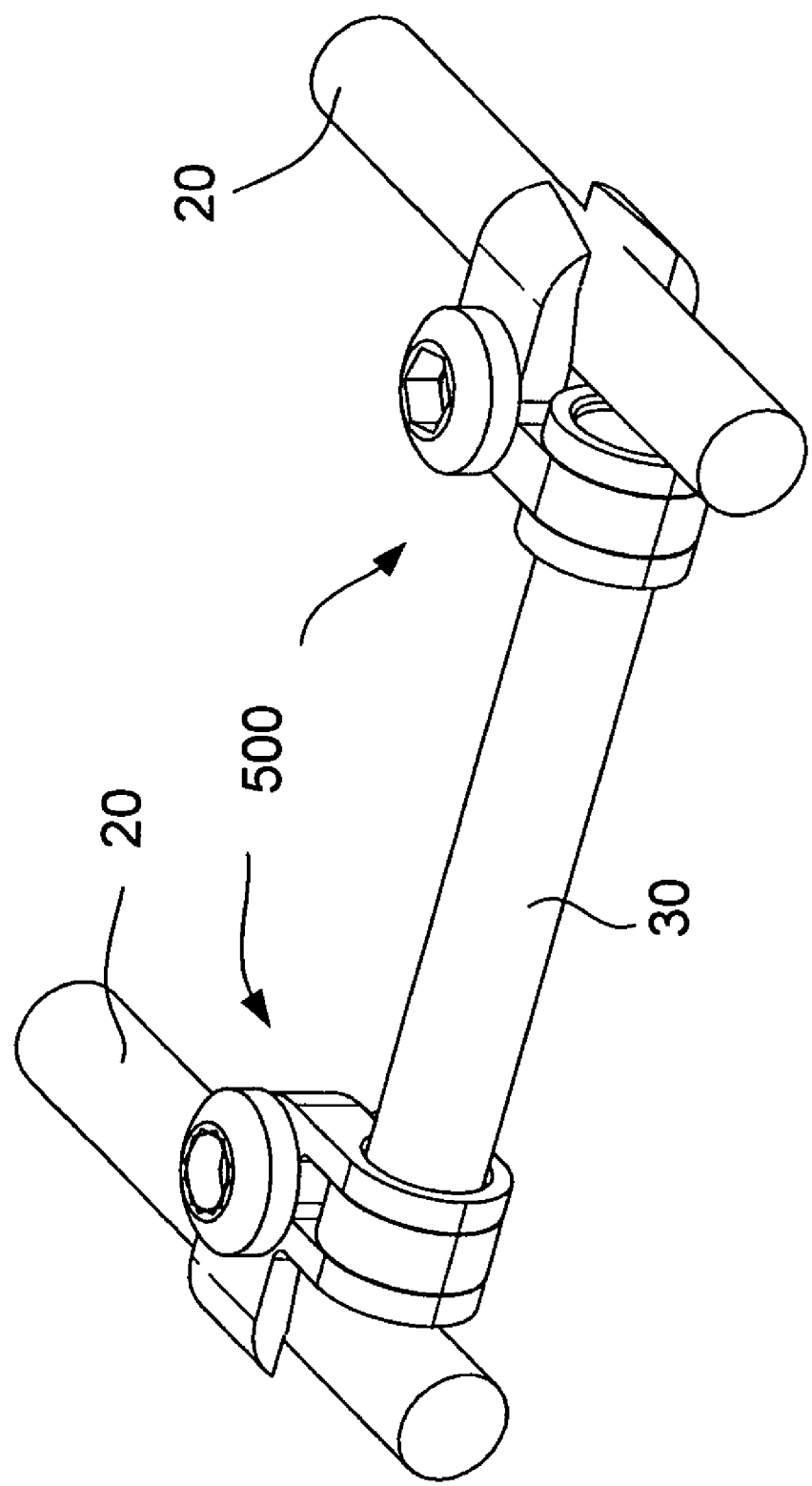
FIG. 24 is a perspective view of an alternative cross-coupling apparatus suitable for use in interconnecting two longitudinal stabilization rods via a transverse stabilization rod.

As also illustrated in FIG. 18, the stabilization rods 20 may also be coupled to one another by way of a cross coupling apparatus 60. The cross coupling apparatus 60 is shown in another perspective view in FIG. 24. Like the apparatus 50 and 50A, the cross coupling apparatus 60 permits a cross connection between the stabilization rods 20 before or after they are fixed to the bone anchors 100. The cross coupling apparatus 60 includes a pair of transverse rod clamps 500 and a transverse rod 30.

Figure 25:
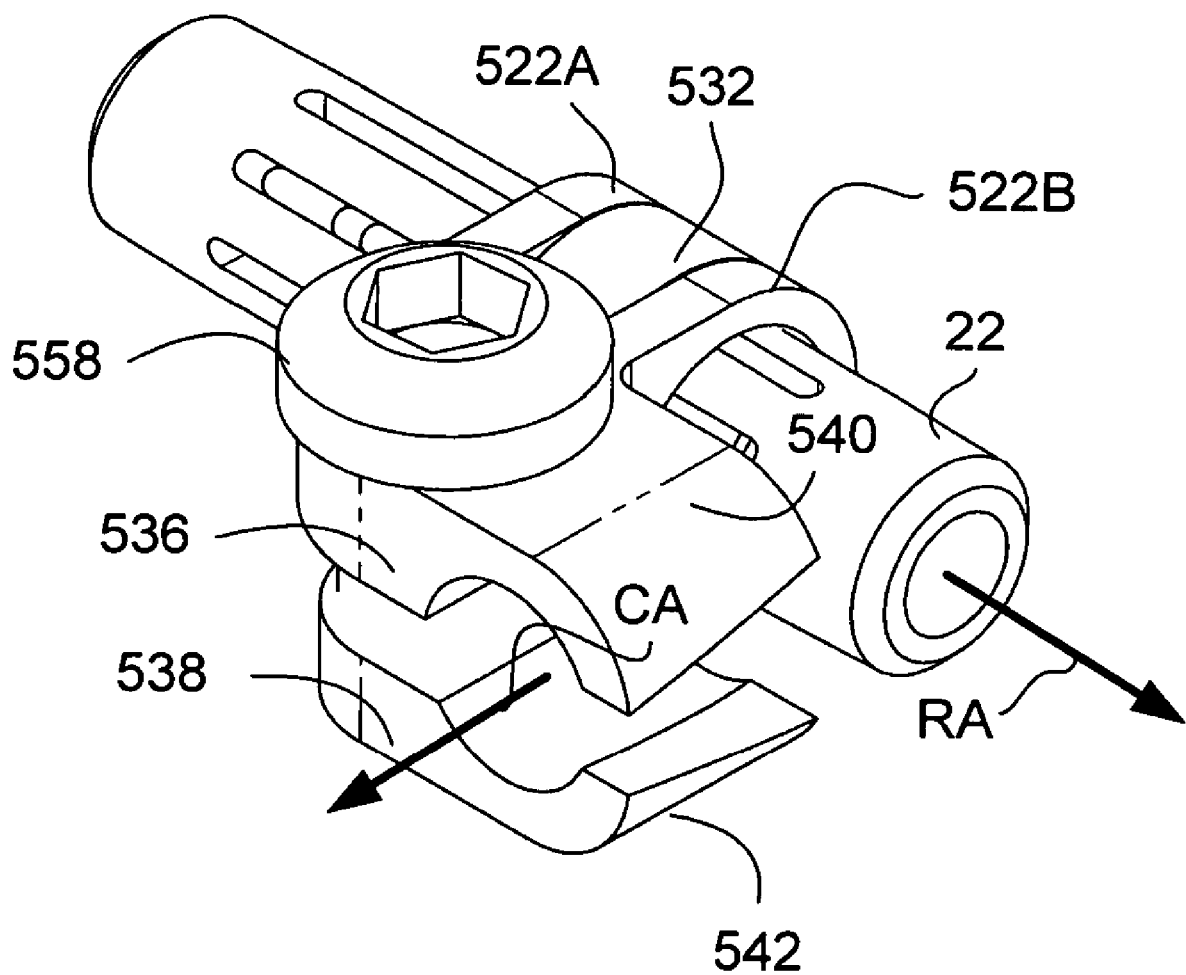
FIG. 25 is a perspective view of a transverse rod clamp of the cross-coupling apparatus of FIG. 24.
Figure 26B:
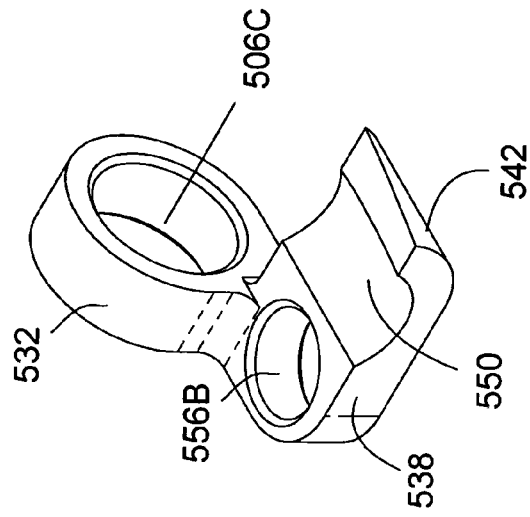
FIG. 26B is a perspective view of another portion of the transverse rod clamp of FIG. 25.
Figure 26A:
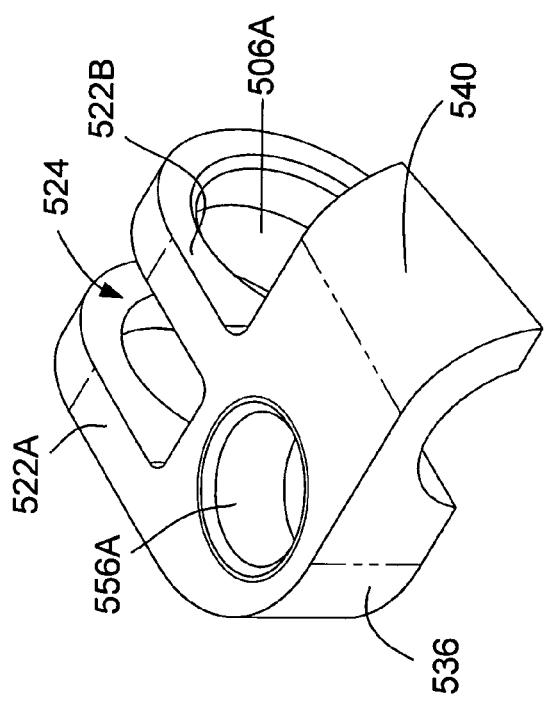
FIG. 26A is a perspective view of a portion of the transverse rod clamp of FIG. 25.
Figure 27:
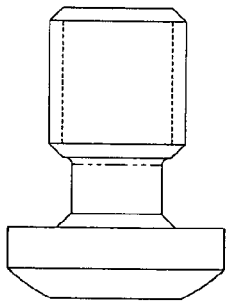
FIG. 27 is a side view of a locking element for the transverse rod clamp of FIG. 25.

As illustrated in FIGS. 25, 26A and 26B, and 27, the transverse rod clamps 500 share some similar features with transverse rod clamps 400 discussed hereinabove. The transverse rod clamps 500, however, also include one or more additional features which will be discussed hereinbelow. As illustrated in FIG. 25, the transverse rod clamp 500 may be provided as a pre-assembly for use by a surgeon by placing the insert 22 in the passage 506 in order to keep the components of the clamp 60 from becoming disengaged.

The transverse rod clamp 500 includes a first pivot element 502, and a second pivot element 504 that cooperate to interconnect the longitudinal stabilization rod 20 to the transverse stabilization rod 30. The first and second pivot elements 502, 504 are adapted to produce a passage 506 through which the transverse stabilization rod 30 may slide. Thus, as with the transverse rod clamp 400, the surgeon may position the transverse rod clamp 500 along the transverse stabilization rod 30 and then manipulate the passage 506 (via the locking mechanism 508) such that it does not permit the transverse stabilization rod 30 to slide within the transverse rod clamp 500, thereby fixing the transverse rod clamp 500 with respect to the rod 30. The locking mechanism 508 is also operable to simultaneously cause a rod engagement mechanism 510 to clamp to the longitudinal stabilization rod 20 to fix the transverse rod clamp 500 thereto.

As with the transverse rod clamp 400, the first pivot element 502 includes a body 520 having wall members 522A, 522B that are spaced apart such that they define a recess, gap, or space 524 within the body 520. The second pivot element 504 also includes a body 530, preferably having a single wall member 532, where the wall member 532 is disposed in the space 524 of the second pivot element 502 such that the apertures 506A, 506B, and 506C are in substantial axial alignment and cooperate to form the passage 506 for receiving the transverse stabilization rod 30.

The rod axis RA is axially aligned with a central axis of transverse stabilization rod 30 disposed within the apertures. The rod axis RA of the transverse rod clamp 500 is generally transverse to the central axis CA of the longitudinal stabilization rod 20.

The locking mechanism 508 includes respective locking elements 536, 538, which depend from the respective bodies 520, 530 of the first and second pivot elements 502, 504. Although each of the locking elements 536, 538 may urge the respective pivot elements 502, 504 to rotate about the transverse stabilization rod 30 and about the rod axis RA, their primary function is to be drawn toward one another in order to fix the rods 20, 30 together. (This is in contrast to the locking elements 436, 438 of the transverse rod clamp 400.) Thus, the locking elements 536, 538 of the transverse rod clamp 500 operate to cause the inner surfaces 546, 550 of the respective rod engagement elements 540, 542 to engage opposite sides of the longitudinal stabilization rod 20, and to urge the wall members 522A, 522B, and 532 to misalign and clamp the transverse stabilization rod 30 within the passage 506.

Like the transverse rod clamp 400, the locking elements 536, 538 of the transverse rod clamp 500 extend from the respective bodies 520, 530 transversely with respect to the rod axis RA and substantially parallel to the central axis CA of the longitudinal stabilization rod 20. As best seen in FIG. 25, however, the locking elements 536, 538 are disposed on the same side of the respective wall members 522A, 522B, and 532 (and on the same side of the rod axis RA) as the respective rod engagement elements 540, 542. (This is in contrast to the lever arms 536, 538 of the transverse rod clamp 400, which are disposed on an opposite side of the rod axis RA.) The rod engagement elements 540, 542 extend from the respective bodies 520, 530 such that the central axis CA is laterally offset from the apertures 506A, 506B, 506C, in a direction substantially parallel with the transverse rod axis RA.

The locking mechanism 508 may include at least one bore 556 extending through at least one of the lever arms 536, 538.

In this embodiment, each of the first and second lever arms 536, 538 include a bore 556A, 556B, respectively, extending therethrough towards the other lever arm. In the embodiment illustrated, respective bores 556A and 556B are disposed in each locking element 536, 538. In a one embodiment, the bore 556A is not threaded, while the bore 556B is threaded. The locking mechanism 208 also includes a locking element 558 that is operable to engage the bores 556A, 556B and cause the displacement of the lever arms 536, 538 toward one another. Further details of the locking element 558 may be seen in FIG. 27.

In another embodiment, the bore 556B is not threaded, while the bore 556A is threaded. Use of both embodiments in one application permits the locking element 558 of each transverse rod clamp 400 to be directed at least partially toward the surgeon.

Turning again to FIG. 18, one or more of the stabilization rods 20 may also be stabilized by way of a cross coupling apparatus 70A and/or 70B. The cross coupling apparatus 70A, 70B may employ either of the transverse rod clamps 400, 500 discussed above and a hook 80 (instead of the transverse rod 30). The cross coupling apparatus 70A employs a left hand hook 80A (also shown in FIG. 28A). The cross coupling apparatus 70B employs a right hand hook 80B, which is the mirror image of left hand hook 80B. The hooks may be used to engage bone, spinous process, the laminar, etc. of the patient. An alternative design left hand hook 80B is illustrated in FIG. 28B. Alternative cross coupling apparatus 70C and 70D are shown in FIG. 29A, which employ the transverse rod clamps 500 and alternative hook designs, left hand hook 80C (also shown in FIG. 29B) and right hand hook 80C (also shown in FIG. 29C).

Figure 30:
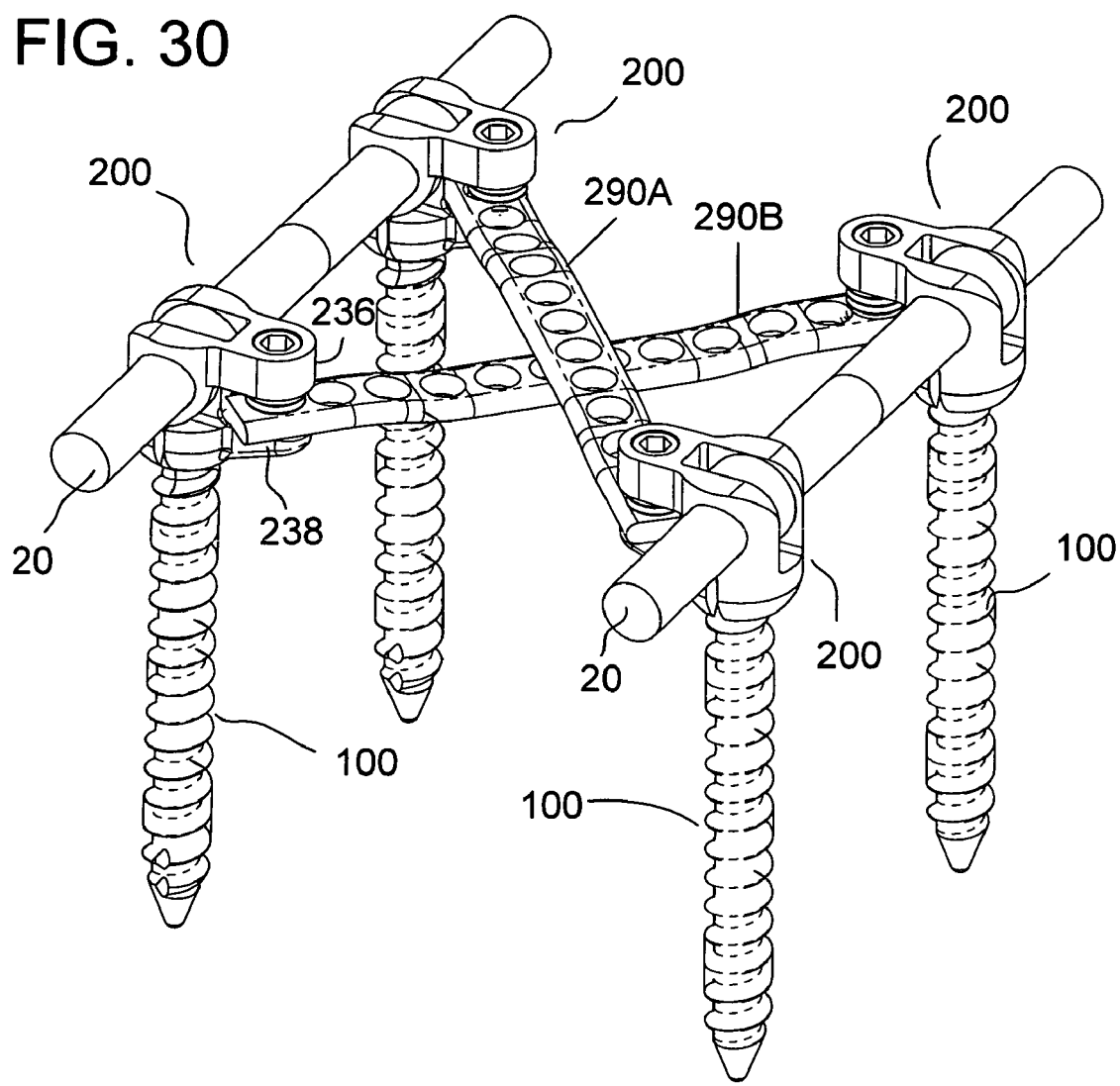
FIG. 30 is a perspective view of a transverse stabilization system that may be employed to couple a pair of longitudinal stabilization rods to one another using transverse beams that are coupled to the tulips of FIG. 1.
Figure 31:
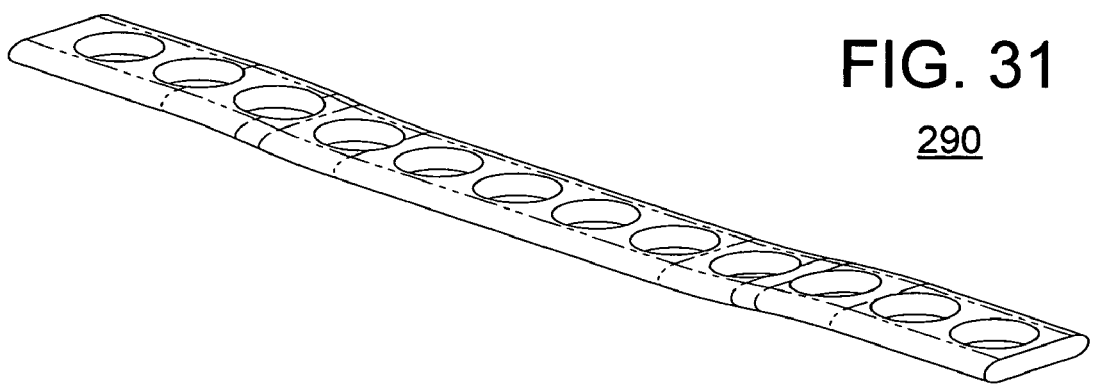
FIG. 31 is a perspective view of one of the transverse beams of FIG. 30.

Reference is now made to FIG. 30, which illustrates an alternative embodiment in which the stabilization system may include two cross-link members 290A, 290B that each extend transversely from, and connects, a pair of tulips 200 in an X-configuration. As also seen in FIG. 31, the cross-link members 290A, 290B are of generally elongate construction having first and second ends and an offset midsection such that they do not interfere with one another where they cross. Recalling from the discussion above that the first and second lever arms 236, 238 are spaced apart defining a gap 260 therebetween, the ends of the cross-link members 290A, 290B are positioned in the respective gaps 260 of the tulips 200. The locking elements 258 are operable to engage the respective cross-link member 290A, 290B and directly or indirectly bias them against the lever arms to: (i) fix the cross-link member 290 to the tulip 200, and (ii) cause the displacement of the first and second lever arms 236, 238.

Figure 32:
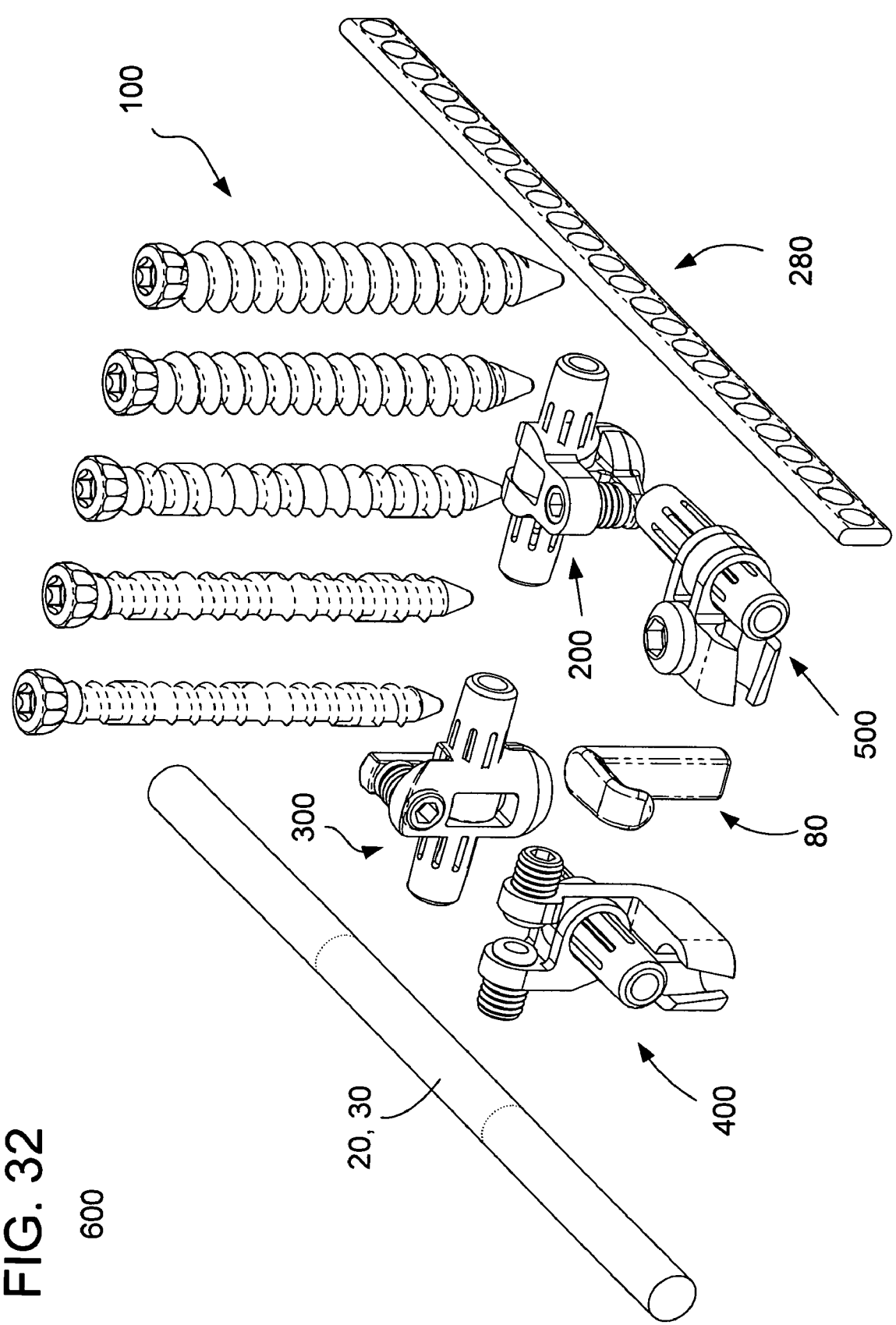
FIG. 32 is a perspective view of kit containing a plurality of stabilization systems and system elements that may be provided to a surgeon during an implantation procedure.

With reference to FIG. 32, the surgeon is preferably provided with a kit 600 including one or more stabilization rods 20, 30 (for longitudinal and/or transverse use), a plurality of bone anchors 100, one or more of the tulips 200, 300, one or more of the cross couplings 400, 500, one or more of the hooks 80, etc., each of which exhibits the same of different physical properties so that the surgeon may customize the stabilization apparatus to the patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A stabilization system for implantation in a patient, comprising:
   a bone anchor including a head and a shaft, the shaft extending away from the head along a bone insertion axis and being operable for connection to a bone of the patient; and
   a tulip including: (i) a first pivot element including a first body having at least one first wall member through which at least one first aperture extends, a first anchor engagement element of the first body including an outer surface and an inner surface, the inner surface including a contour operable to engage the head of the bone anchor and terminating at a first edge, and a first lever arm extending from the first body and forming at least a portion of a first locking element; and (ii) a second pivot element including a second body having at least one second wall member through which at least one second aperture extends, a second anchor engagement element of the second body including an outer surface and an inner surface, the inner surface including a contour operable to engage the head of the bone anchor and terminating at a second edge, and a second lever arm extending from the second body and forming at least a portion of a second locking element, wherein:
   the first and second wall members are disposed adjacent to one another such that the first and second apertures are sized, shaped and disposed in substantial axial alignment, and such that they are operable to receive a stabilization rod therethrough, and
   displacement of the first and second lever arms of the respective first and second locking elements away from one another: (i) urges the first and second wall members to pivot about a central portion of the first and second apertures, (ii) urges the first and second apertures to misalign and thereby clamp the stabilization rod, and (iii) causes the first pivot element and the second pivot element to pivot in opposite directions about the stabilization rod thereby creating a corresponding movement of the first and second anchor engagement elements toward one another such that the respective inner surfaces of the first and second anchor engagement elements are directed toward one another to engage opposite sides of the head of the bone anchor, thereby clamping the head of the bone anchor therebetween.

2. The stabilization system of claim 1, wherein displacement of the first and second lever arms causes the first and second wall members to pivot about, and clamp, the stabilization rod.

3. The stabilization system of claim 1, wherein:
   at least one of the first and second lever arms includes a bore extending therethrough towards the other of the at least one of the first and second lever arms; and
   the stabilization system further includes a locking element operable to engage the bore and cause the displacement of the first and second lever arms by direct or indirect engagement with the other of the at least one of the first and second lever arms.

4. The stabilization system of claim 3, wherein the bore is threaded and the locking element includes a threaded shaft having first and second ends, the first end extending toward and engaging the other of the at least one of the first and second lever arms, the threaded shaft causing the displacement of the first and second lever arms in response to turning through the bore.

5. The stabilization system of claim 1, wherein:
the first body includes at least two first wall members in a spaced apart orientation, each first wall member including a first aperture therethrough; and
the second body includes one second wall member disposed in the space between the at least two first wall members,
wherein the first apertures and the second aperture are in substantial axial alignment, with the second aperture located between the first apertures.

6. The stabilization system of claim 1, wherein:
the first and second lever arms are spaced apart defining a gap therebetween; and
the stabilization system further comprises a cross-link member of generally elongate construction having first and second ends, at least one of the first and second ends being positioned in the gap.

7. The stabilization system of claim 6, wherein the second end of the cross-link member being operable to couple to another stabilization system.

8. The stabilization system of claim 6, wherein:
the first lever arm includes a bore extending therethrough towards the second lever arm;
the stabilization system further includes a locking element operable to engage the bore and extend into the gap; and
the locking element is operable to engage the cross-link member and directly or indirectly bias against the second lever arm to: (i) fix the cross-link member to the tulip, and (ii) cause the displacement of the first and second lever arms.

9. The stabilization system of claim 8, wherein the cross-link member includes at least one aperture therethrough sized and shaped to engage locking element.

10. The stabilization system of claim 1, wherein:
the inner surfaces of the first and second anchor engagement elements define an inner volume operable to receive the head of the bone anchor to achieve various articulations of the tulip about the head;
the first and second edges define an aperture through which the bone anchor may extend out of the inner volume; and
the inner volume and the aperture are positioned along the bone insertion axis.

11. The stabilization system of claim 10, wherein displacement of the first and second lever arms cause at least portions of the inner surfaces of the first and second anchor engagement elements to engage the head of the bone anchor to fix the tulip to the bone anchor.

12. The stabilization system of claim 10, wherein displacement of the first and second lever arms cause at least portions of the inner surfaces of the first and second anchor engagement elements to engage the head of the bone anchor to fix the tulip to the bone anchor.

13. The stabilization system of claim 12, wherein the head of the bone anchor includes a friction enhancement feature.

14. The stabilization system of claim 13, wherein the friction enhancement feature includes at least one of ridges, grooves, protrusions, dimples, crosshatching, and knurling.

15. The stabilization system of claim 10, wherein:
the first and second apertures define a rod axis therethrough, which is axially aligned with a central axis of the stabilization rod when disposed within the apertures; and
the rod axis is generally transverse to the bone insertion axis.

16. The stabilization system of claim 15, wherein:
the first lever arm extends from the first body transversely with respect to both the rod axis and the bone insertion axis; and
the second lever arm extends from the second body transversely with respect to both the rod axis and the bone insertion axis.

17. The stabilization system of claim 16, wherein at least one of the first and second lever arms extends substantially perpendicularly from the first and second bodies, respectively.

18. The stabilization system of claim 15, wherein:
the first lever arm extends from the first body transversely with respect to the rod axis and substantially parallel with respect to the bone insertion axis; and
the second lever arm extends from the second body transversely with respect to the rod axis and substantially parallel with respect to the bone insertion axis.

19. A stabilization rod engaging apparatus for implantation in a patient, comprising:
a first pivot element including a first body having at least one first wall member through which at least one first aperture extends, a first anchor engagement element of the first body including an outer surface and an inner surface, the inner surface including a contour operable to engage a head of a bone anchor and terminating at a first edge, and a first lever arm extending from the first body and forming at least a portion of a first locking element; and
a second pivot element including a second body having at least one second wall member through which at least one second aperture extends, a second anchor engagement element of the second body including an outer surface and an inner surface, the inner surface including a contour operable to engage the head of the bone anchor and terminating at a second edge, and a second lever arm extending from the second body and forming at least a portion of a second locking element, wherein:
the first and second wall members are disposed adjacent to one another such that the first and second apertures are sized, shaped and disposed in substantial axial alignment, and such that they are operable to receive the stabilization rod therethrough, and
displacement of the first and second lever arms of the respective first and second locking elements away from one another: (i) urges the first and second wall members to pivot about a central portion of the first and second apertures, (ii) urges the first and second apertures to misalign and thereby clamp the stabilization rod, and (iii) causes the first pivot element and the second pivot element to pivot in opposite directions about the stabilization rod thereby creating a corresponding movement of the first and second anchor engagement elements toward one another such that the respective inner surfaces of the first and second anchor engagement elements are directed toward one another, and such that they are operable to clamp the head of the bone anchor therebetween.

20. The stabilization rod engaging apparatus of claim 19, the first and second engagement elements are operable to engage a stabilization member for extension in a transverse direction relative to the stabilization rod in response to the displacement of the first and second locking elements relative to one another.

21. A method, comprising: providing a first pivot element including a first body having at least one first wall member through which at least one first aperture extends, a first anchor engagement element of the first body including an outer surface and an inner surface, the inner surface including a contour operable to engage a head of a bone anchor and terminating at a first edge, and a first lever arm extending from the first body and forming at least a portion of a first locking element;

providing a second pivot element including a second body having at least one second wall member through which at least one second aperture extends, a second anchor engagement element of the second body including an outer surface and an inner surface, the inner surface including a contour operable to engage the head of the bone anchor and terminating at a second edge, and a second lever arm extending from the second body and forming at least a portion of a second locking element; and disposing the first and second wall members adjacent to one another such that the first and second apertures such that they are in substantial axial alignment and are operable to receive a stabilization rod therethrough, wherein:

displacement of the first and second lever arms of the respective first and second locking elements away from one another: (i) urges the first and second wall members to pivot about a central portion of the first and second apertures, (ii) urges the first and second apertures to misalign and thereby clamp the stabilization rod, and (iii) causes the first pivot element and the second pivot element to pivot in opposite directions about the stabilization rod thereby creating a corresponding movement of the first and second anchor engagement elements toward one another such that the respective inner surfaces of the first and second anchor engagement elements are directed toward one another to engage opposite sides of the head of the bone anchor and are operable to clamp the head of the bone anchor.

22. The method of claim 21, further comprising:
implanting the first and second pivot elements and a stabilization rod in a patient; and
displacing the first and second locking elements relative to one another such that the first and second apertures clamp the stabilization rod.

23. The method of claim 22, further comprising:
implanting a bone anchor in a bone of the patient; and
displacing the first and second locking elements relative to one another such that the first and second engagement elements engage the head of the bone anchor and fix the stabilization rod to the bone anchor.

24. The method of claim 21, wherein the first and second anchor engagement elements are operable to engage a bone anchor for extension in a transverse direction relative to a stabilization rod in response to the displacement of the first and second locking elements relative to one another.

25. The method of claim 24, further comprising:
implanting the bone anchor in a patient; and displacing the first and second locking elements relative to one another such that the first and second anchor engagement elements engage the bone anchor and fix the bone anchor to the stabilization rod.

26. A stabilization system for implantation in a patient, comprising:
a bone anchor including a head and a shaft, the shaft extending away from the head along a bone insertion axis and being operable for connection to a bone of the patient; and
a tulip including: (i) a first pivot element including a first body having at least one first wall member through which at least one first aperture extends, a first anchor engagement element of the first body including an outer surface and an inner surface, the inner surface including a contour operable to engage the head of the bone anchor and terminating at a first edge, and a first lever arm extending from the first body and forming at least a portion of a first locking element; and (ii) a second pivot element including a second body having at least one second wall member through which at least one second aperture extends, a second anchor engagement element of the second body including an outer surface and an inner surface, the inner surface including a contour operable to engage the head of the bone anchor and terminating at a second edge, and a second lever arm extending from the second body and forming at least a portion of a second locking element, wherein:
the first and second wall members are disposed adjacent to one another such that the first and second apertures are sized, shaped and disposed in substantial axial alignment, and such that they are operable to receive a stabilization rod therethrough, and
displacement of the first and second lever arms of the respective first and second locking elements away from one another (i) urges the first and second wall members to pivot about a central portion of the first and second apertures, (ii) urges the first and second apertures to misalign and thereby clamp the stabilization rod, and (iii) directs the respective inner surfaces of the first and second anchor engagement elements toward one another to engage opposite sides of the head of the bone anchor, thereby clamping the head of the bone anchor therebetween.

* * * * *